United States Patent
Papoutsakis et al.

(10) Patent No.: US 11,820,968 B2
(45) Date of Patent: Nov. 21, 2023

(54) MEGAKARYOCYTIC PARTICLES AND MICROPARTICLES FOR IN VIVO HEMATOPOIETIC CELL AND GENE THERAPIES

(71) Applicants: Eleftherios Papoutsakis, Newark, DE (US); Chen-Yuan Kao, Newark, DE (US); Jinlin Jiang, Gaithersburg, MD (US)

(72) Inventors: Eleftherios Papoutsakis, Newark, DE (US); Chen-Yuan Kao, Newark, DE (US); Jinlin Jiang, Gaithersburg, MD (US)

( * ) Notice: Subject to any disclaimer, the term of this patent is extended or adjusted under 35 U.S.C. 154(b) by 269 days.

(21) Appl. No.: 16/711,396

(22) Filed: Dec. 11, 2019

(65) Prior Publication Data

US 2020/0115681 A1  Apr. 16, 2020

Related U.S. Application Data

(62) Division of application No. 15/308,221, filed as application No. PCT/US2015/031388 on May 18, 2015, now Pat. No. 10,538,738.

(60) Provisional application No. 62/000,109, filed on May 19, 2014.

(51) Int. Cl.
  *A61K 35/19* (2015.01)
  *C12N 5/078* (2010.01)
  *A01N 1/02* (2006.01)

(52) U.S. Cl.
  CPC .......... *C12N 5/0644* (2013.01); *A01N 1/0226* (2013.01); *A61K 35/19* (2013.01); *C12N 2521/00* (2013.01)

(58) Field of Classification Search
  CPC .. C12N 2521/00; C12N 5/0644; A61K 35/19; A01N 1/0226
  See application file for complete search history.

(56) References Cited

U.S. PATENT DOCUMENTS

| | | | |
|---|---|---|---|
| 5,093,045 A | 3/1992 | Shoyab | |
| 2001/0005591 A1 | 7/2001 | Qasba | |
| 2004/0152628 A9 | 8/2004 | Tandon | |
| 2005/0277187 A1 | 12/2005 | Johnson | |
| 2006/0141461 A1 | 6/2006 | Keefe | |
| 2008/0069807 A1* | 3/2008 | Jy et al. | 424/93.72 |
| 2011/0294737 A1 | 12/2011 | Schwertz | |
| 2012/0014933 A1* | 1/2012 | Baruch et al. | 424/93.72 |
| 2012/0238020 A1 | 9/2012 | Mitchell | |
| 2012/0315338 A1 | 12/2012 | Li | |
| 2012/0321723 A1* | 12/2012 | Bruno et al. | 424/553 |
| 2014/0100138 A1 | 4/2014 | Botvinick | |

FOREIGN PATENT DOCUMENTS

| | | |
|---|---|---|
| WO | 2010/121122 A2 | 10/2010 |
| WO | 2013/043860 A1 | 3/2013 |

OTHER PUBLICATIONS

Ratajczak et al., "Embryonic stem cell-derived microvesicles reprogram hematopoietic progenitors: evidence for horizontal transfer of mRNA and protein delivery", Leukemia, 2006, vol. 20, No. 5, pp. 847-856. (Year: 2006).*
Dunois-Larde, C., et al., Exposure of human megakaryocytes to high shear rates accelerates platelet production. Blood, 2009. 114(9): p. 1875-1883.
Jiang, J., D.S. Woulfe, and E.T. Papoutsakis, Shear enhances thrombopoiesis and formation of microparticles that Induce megakaryocytic differentiation of stem cells. Blood, 2014. 124(13): p. 2094-103.
Schlinker, A.C., et al., Separation of In-Vitro-Derived Megakaryocyles and Platelets Using Spinning-Membrane Filtration. Biotechnology and Bioengineering, 2015. 112(4): p. 788-800.
Richard A. Nash, Ted Gooley, Chris Davis, Frederick R. Appelbaum, The Problem of Thrombocytopenia after Hematopoietic Stem Cell Transplantation, The Oncologist, vol. 1, Issue 6, Dec. 1996, pp. 371-380, https://doi.org/10.1634/theoncologist.1-6-371.
Edwin van der Pol, Anita N. Boing, Paul Harrison, Augueste Sturk and Rienk Nieuwland Mark P. Mattson, Associate Editor Pharmacological Reviews Jul. 2012, 64 (3) 676-705; DOI: https://doi.org/10.1124/pr.112.005983.
A doxorubicin delivery platform using engineered natural membrane vesicle exosomes for targeted tumor therapy. (Feb. 2014) Tian, YH; Li, SP; Song, J; Ji, TJ; Zhu, MT; Anderson, GJ ; Wei, JY; Nie, GJ. Biomaterials vol. 35 p. 2383-2390. DOI10.1016/j.biomaterials.2013.11.083.
Flaumenhaft et al., "Megakaryoctye-derived microparticles: direct visualization and distinction from platelet-derived microparticles", Blood, Jan. 29, 2009, vol. 113(5), pp. 1112-1121.

* cited by examiner

*Primary Examiner* — Satyendra K Singh
(74) *Attorney, Agent, or Firm* — RatnerPrestia

(57) ABSTRACT

Applications in transfusion medicine requiring platelets, and hematopoietic stem-cell transplantations require either platelets or enhancement of in vivo platelet biogenesis. Gene therapy applications of hematopoietic stem and progenitor cells (HSPCs) require effective and specific modification of HSPCs by DNA, RNA or other biological molecules. Here we disclose methods for the generation, and modification of megakaryocytic microparticles (MkMPs), proplatelets, pre-platelets, platelet-like particles and megakaryocyte extracellular vesicles, that can be used in the aforementioned transfusion and transplantation medicine applications and in gene therapy applications involving hematopoietic stem cells. The biological effects of modified or unmodified MkMPs have never been previously disclosed and thus, this invention claims all biological applications of MkMPs in in vivo therapeutic applications to produce various cells and cell parts, modify various target cells or deliver molecules including drugs to HSPCs and related cells.

26 Claims, 24 Drawing Sheets

MEGAKARYOCYTIC PARTICLES AND MICROPARTICLES FOR IN VIVO HEMATOPOIETIC CELL AND GENE THERAPIES

CROSS-REFERENCE TO RELATED APPLICATION

This application is a divisional of U.S. patent application Ser. No. 15/308,221 filed on Nov. 1, 2016, currently pending and herein incorporated by reference; which is the 371 U.S. National stage of International Application PCT/US2015/031388 filed on May 18, 2015, which claims the benefit of U.S. Provisional Application No. 62/000,109, filed on May 19, 2014, the contents of which are incorporated herein by reference.

REFERENCE TO U.S. GOVERNMENT SUPPORT

This work is supported by a grant from the National Institutes of Health (Award No. R21HL106397). The United States has certain rights in the invention.

FIELD OF THE INVENTION

The invention relates to the generation and use of megakaryocytic microparticles (MkMPs), extracellular vesicles, platelet-like particles (PLPs) and proplatelets/preplatelets (PPTs) that are produced from mature and immature megakaryocytes. Megakaryocytes can be produced from human hematopoietic stem and progenitor cells (HSPCs) but also from embryonic stem and induced pluripotent stem (iPS) cells. The present invention relates to all applications of MkMPs in transfusion medicine, hematopoetic-cell transplantation and for delivering DNA, RNA, protein and other molecules to HSPCs (hematopoietic stem/progenitor cells) that can be obtained from various sources including the bone marrow, the peripheral blood, cord blood or from embryonic or iPS cells. The present invention also relates to methods for using biomechanical forces as a mean to increase the number of PLPs, PPTs and MkMPs that can be generated from megakaryocytes.

BACKGROUND OF THE INVENTION

Megakaryocytes (Mks) are derived from hematopoietic (blood) stem cells (typically contained in the $CD34^+$ compartment), and are distinguished by their very large size, high DNA content, and the formation of proplatelet extensions which shed platelets, the small cells necessary for blood coagulation. Mk cells differentiate in the bone-marrow (BM) vasculature: they undergo a variation of the normal cell cycle, termed endomitosis, to form polyploid cells ($\geq 8N$ DNA content). Committed Mks migrate from the hematopoietic compartment of BM towards the endothelial lining of the BM sinusoids where they mature and extend long, branched cytoplasmic protrusions termed proplatelets through gaps of the endothelium into the vasculature. Mk cells encounter mechanical stresses as they deform to penetrate the gaps of the sinusoid walls, and shear forces by the exposure to blood flow. The pulmonary circulation is another important site of Mk maturation and platelet biogenesis: Mks may enter the BM circulation and reach the lungs where they shed proplatelets. As such, Mk cells encounter shear forces in circulation as well as mechanical strain in the lung vasculature. Thus, Mk maturation and platelet release appear to be stress-induced processes. However, the cellular/molecular events underlying the effects of mechanical stresses on Mk maturation and platelet biogenesis remain unexplored from the fundamental and practical applications point of view.

Platelets are an expensive product in limited supply. This is due to the collection and processing steps from donated blood, and the fact that platelets cannot be frozen, but also due to the possibility of bacterial or blood-borne pathogen contamination, and of alloimmunization of recipients. As was recently reviewed and argued, culture-derived platelets, produced under Good Manufacturing Practices, hold a great potential for providing an abundant, safer and more tolerated platelet supply for transfusion therapies. However, major advances are needed for large-scale, culture-based platelet production to become economically attractive. This will require improvements in the expansion of $CD34^+$ cells into Mks, and the ability to produce large, polyploid Mk cells, since the number of platelets produced is proportional to the cell ploidy. As Mk maturation is also affected by interactions with stroma and extracellular matrix, platelet production will need to engage bioreactor systems involving semi-synthetic matrices under controlled flow conditions to simulate, to the extent possible, in vivo conditions.

In addition to platelet transfusions, there is a need to enhance platelet biogenesis in patients with thrombotic deficiency or excessive bleeding due to trauma, also in patients undergoing chemotherapy treatment for cancer due to the fact that chemotherapy destroys the ability of the body to produce platelets. In vitro production of functional proplatelets/platelets is firmly established. Thus, culture-derived Mks or platelets could provide a safer and more tolerated supply for transfusion therapies greatly impacting a very large community of patients in the US and worldwide. Calculations suggest that generation of clinically-relevant doses of functional platelets is possible, but key scientific and technological challenges remain. First, expansion of hematopoietic stem cells without loss of Mk-differentiation potential, and then production of a larger number of Mks per input $CD34^+$ cell will require substantial improvements. Second, because the degree of ploidy directly correlates with the number of platelets produced, it is necessary to increase the ploidy of cultured Mks similar to what is observed in vivo, thus making it possible to obtain several thousand platelets per Mk.

For patients undergoing ablative chemotherapy or those with certain genetic disorders, there is a need for hematopoietic stem and progenitor cell (HSPCs) transplantation to reconstitute the hematopoietic system that is destroyed by chemotherapy. The HSPCs are either autologous (collected from the patient prior to chemotherapy) or from a matched donor or from umbilical cord blood. Thus, there is a large need of HSPCs for such therapies and any processes that reduces the number of HSPCs needed for transplantation would have a huge impact on transplantation. Finally, there is a large need to develop reliable gene-therapy technologies that would allow the modification of a patient's HSPCs in order to correct genetic disorders.

The disclosed invention has great translational potential for the development of transformational technologies in transfusion medicine, stem-cell transplantation and gene and related therapies involving HSPCs.

Mks derive from HSPCs in the BM, and as they mature they migrate to the endothelial lining of BM sinusoids where they extend PPTs through gaps of the endothelium into circulation. Mks encounter biomechanical stresses as they deform to penetrate gaps of the sinusoid wall, and shear stresses upon exposure to blood flow. Upon entering circulation, Mk fragments or whole Mks are exposed to shear stresses of a broad range and duration in different parts of circulation. Released Mk fragments mature into platelets in circulation, while released whole Mks are eventually captured in the pulmonary vasculature where they give rise to platelets.

Following pioneering visualization studies [1] identifying a physiological shear-stress range of 1.3-4.1 dyn/cm$^2$ for platelet biogenesis in the BM, a role for shear stress was supported by an in vitro study [4] demonstrating that a high shear rate (1800 s$^{-1}$; corresponding to ca. 16 dyn/cm$^2$, almost 4-fold higher than the upper physiological limit in the BM) accelerates (but was not shown if it increases) PPT formation and platelet biogenesis from cultured, mature Mks. Yet, the cellular events underlying the effects of mechanical stresses on Mk maturation and platelet biogenesis remain largely unexplored. Shear and other biomechanical stresses affect different cell types in biologically multifaceted and complex ways. E.g., shear stress is an important differentiation signal for embryonic stem cells, endothelial progenitor cells circulating in peripheral blood, and mesenchymal stem cells. Many cellular processes are affected by shear forces, including the cell cycle, migration, apoptosis and differentiation.

Cell-derived microparticles (MPs also known as microvesicles; MVs) are membrane-bound vesicles with diameter from 100 to 1000 nm and can be derived from almost all types of cells by direct budding from plasma membrane. They are different from exosomes (<100 nm), which originate from multivesicular bodies through cell exocytosis.

MP generation is always associated with cell growth, and some type of stimulus which could be cell activation or some kind of stress stimulus. Different stimuli have been reported for different cell types for the generation of MPs. A very wide range of stimuli can induce cells to produce MPs in vitro, including different types of physicochemical stress (e.g., shear, hypoxia and oxidative stress), physiological activators (e.g., thrombin, Fas ligand and tumor necrosis factor alpha) and non-physiological agonists (e.g., lipopolysaccharide and calcium ionophore A23187). Upon stimulation, cells undergo activation or apoptosis and different amount of MPs are released from different types of cells. The released MPs are heterogeneous with respect to their surface marker expression, membrane phospholipid composition, and internal RNA and protein repertoires as well as their biological activities even when they are from the same parent cells but generated under different stimulation conditions. There is no universal mechanism leading to MP release. Cytosolic Ca$^+$ elevation, oxidative stress, cytoskeleton reorganization, caspase activation and lipid raft are involved in MP biogenesis.

MPs exert various and diverse biological effects on target cells, and this variety depends largely on the variety of bioactive molecules carried by MPs. It has been shown that surface markers, proteins, mRNA, microRNA, DNA or even phospholipid can act as signaling molecules inside target cells. For example, MPs from G-CSF-activated primary monocytes or PMA-stimulated THP-1 monocytic cells induced differentiation of monocytes into macrophages and this process was mediated by miR-223 transfer [2]. Under many conditions, the biological function of MPs is not mediated simply by one type of signaling molecules. Several mechanisms, including MP attachment to cells, direct fusion and endocytosis, have been proposed and examined by studies to explain uptake process of MPs by target cells.

The biological function of MPs during intercellular communication is dependent on the interaction of MPs with and subsequently transmission of signaling to target cells. Three different types of MP-cell interaction have been demonstrated. Binding of MPs to cells is the first step of interaction and several studies have demonstrated this process could be target-specific. For example, platelet-derived microparticles (PMPs) could transfer tissue factor to monocytes but not to neutrophils though PMPs could adhere to both types of cells through CD62P. In some cases, MP binding is sufficient to alter the fate of target cells through activation of receptors on the target cells via the corresponding ligands present on the MP surface. MPs from endothelial cells, monocytes, platelets or human blood could bind to platelets through exposed phosphatidylserine on MPs and its receptor CD36 on platelets, and this CD36-dependent binding event augmented platelet activation in response to low dose of ADP [3]. In some cases, MPs are taken up by target cells following binding through two distinct mechanisms: membrane fusion and endocytosis. Both mechanisms could lead to membrane receptor transfer and internal "cargo" discharge into the target cells. PMPs were internalized by human brain endothelial cells through active endocytosis and this led to modified endothelial cell phenotype and functions.

Chinese patent CN 104195107A discloses the application of microvesicles from activated platelets in megakaryocytic differentiation of stem cells. Part of the present invention discloses the use of megakaryocytic microparticles in inducing megakaryocytic differentiation of hematopoietic stem cells and in ex vivo platelet production. CN 104195107A uses microvesicles from activated platelets, and thus these are NOT MkMPs. Equally important, although they discuss that the MPs they produce from activated platelets enhance the megakaryocytic differentiation of HSPCs, they add thrombopoietin, the primary cytokine that induce megakaryocytic differentiation, in the culture medium for stem cells in the invention (CN 104195107A) while the present invention does not require thrombopoietin. Thus, the present invention is distinct from this invention in CN 104195107A. One will see below that the present invention uses MkMPs from megakaryocytes that we have shown above are very different from the MPs from activated platelets, which we show that in the absence of TPO cannot induce megakaryocytic differentiation of HSPCs as shown in FIG. 9 and FIG. 12.

SUMMARY OF THE INVENTION

The present invention relates to shear stress enhancing DNA synthesis, polyploidization and apoptosis of immature megakaryocytic cells (Mk cells), and increases the formation of platelet-like particles (PLPs), pro/preplatelets (PPTs), and Mk microparticles (MkMPs). In addition, shear accelerates DNA synthesis of immature Mks in an exposure-time and shear stress level dependent manner. Both early (phosphatidylserine exposure) and late (caspase-3 activation) apoptotic events were enhanced by shear stress. Inhibition of caspase-3 reduced the number of shear-induced PLP/PPT and MkMP formation. Exposure to physiological shear enhances PLP/PPT formation by up to 10.8 fold. PLPs generated under shear flow displayed improved functionality as assessed by CD62P exposure and fibrinogen binding. MkMP generation was dramatically enhanced (up to 47 fold) by shear stress. Significantly, coculture of MkMPs with hematopoietic stem and progenitor cells (HSPCs) promoted HSPC differentiation to mature Mks synthesizing alpha- and dense-granules and forming proplatelets in the absence of exogenous thrombopoietin, thus identifying, for the first time, a novel and unexplored potential physiological role for MkMPs. Through light, transmission or scanning electron microscopy analysis, it is seen that MkMPs could fuse and then transfer internal "cargo" into HSPCs. We show that RNase treatment destroys the endogenous RNA (as shown by decreased effect of MkMPs on HSPCs) and that MkMPs can be loaded desirable molecules for delivery to HSPCs with effectiveness and specificity.

The present invention discloses that PLP/PPT particles as well as MkMPs generated from various cell types (HPSCs, embryonic or iPS cells) under mechanical stress in laminar flow or turbulent flow in mixed bioreactors can be used in the development of autologous or allogeneic cell therapies to treat thrombocytopenias, as a substitute to platelet transfusions or to enhance HSPC transplantation. We also claim that MkMPs can be used as a means to modify in vitro or in vivo hematopoietic stem and progenitor cells by transferring specific nucleic acids (RNA or DNA molecules) or non-nucleic acid morphogens (proteins or other molecules) to these cells. This process can be used for gene and cell therapies based on HPSCs. It can be also used to determine what molecules result in desirable cell differentiation and morphogenesis of the targeted stem and progenitor cells aiming to achieve desirable phenotypes such as production of different blood cells in vivo or trans-differentiation to other cell types.

The present invention discloses methods to generate large number of particles (PLPs, PPTs) from cultured megakaryocytes (Mks or Mk cells) under shear and other biomechanical forces that lead to biologically active particles for platelet functions.

The present invention also discloses methods to generate large number of Mk microparticles (MkMPs) or Mk microvesicles (MkMVs) from cultured Mk cells under shear and other biomechanical forces that lead to biologically active particles that can be used to transfer biological material (RNA, DNA, proteins and other biological or non-biological components or chemicals) to other cells, including hematopoietic stem and progenitor cells.

The present invention further relates to applications of MkMPs and other particles produced from Mk cells alone or as supplements to hematopoietic stem cells for transplantations (also known as bone-marrow transplantations) to enable or enhance the reconstitution of the hematopoietic system.

The present invention also relates to all biological applications ex vivo or in vivo of MkMPs.

The present invention also relates to methods for loading MkMPs, PLPs and PPTs with exogenous RNA, DNA, proteins and drugs for delivery to target cells.

The present invention also relates to methods for unloading first MkMPs, PLPs, and PPTs from native RNA, DNA and select proteins and non-protein morphogens. These unloaded particles can be loaded subsequently with desirable with exogenous RNA, DNA, proteins and drugs for delivery to target cells.

The present invention also relates to methods using stirred and tubular bioreactors for producing MkMPs, PLPs, PPTs from Mk cells derived from HSPCs or embryonic or iPS cells, but also MPs from other cell types. These bioreactors can be used with controlled levels of biomechanical forces to maximize the production of various biological particles.

DETAILED DESCRIPTION

Figure 1:
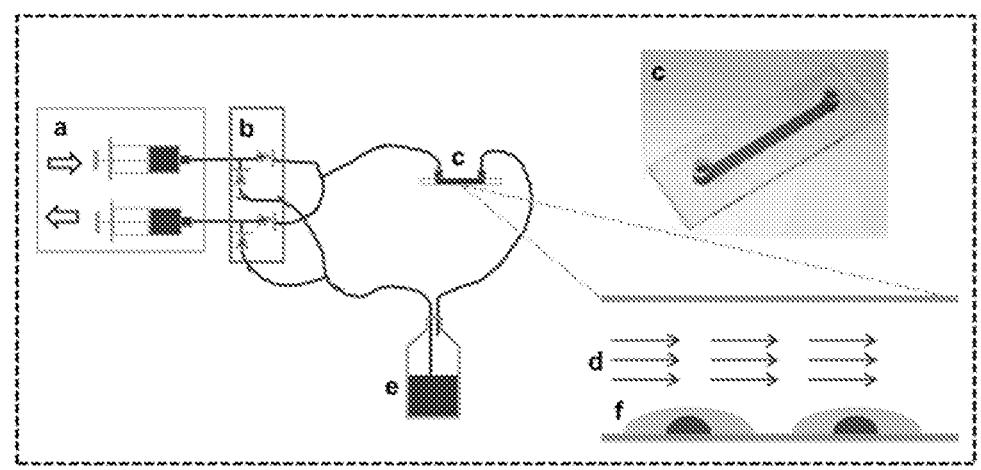
FIG. 1. Sketch of the flow system used to expose Mk cells to shear flow by continuously perfusing medium over Mks attached to flow slides. a, two infusion and withdraw syringe pumps; b, dual check valves; c, extracellular matrix-coated flow slide; d, medium flow; e, medium reservoir; f, Mks.

While the present disclosure may be susceptible to embodiments in different forms, and herein various embodiments will be described in detail with the understanding that the present description is to be considered an exemplification of the principles of the disclosure and is not intended to be exhaustive or to limit the disclosure to the details of construction and the arrangements of the components set forth in the following description or illustrated in the drawings.

Methods Used for the Disclosure and Enablement of the Invention

Materials and Proteins:

All chemicals were obtained from Sigma-Aldrich or otherwise indicated. Recombinant human interleukin 3 (IL-3), IL-6, IL-9, IL-11, stem cell factor (SCF), granulocyte colony-stimulating factor (rhG-CSF) and thrombopoietin (TPO) were from purchased from PeproTech Inc. Purified human von Willbrand Factor (vWF, Factor VIII free) was from Haematologic Technologies. Human fibrinogen for coverslip coating was from Innovative Research. Alexa Fluor® 647-conjugated fibrinogen for platelet functionality assays was from Life Technologies. Phycoerythrin (PE)-conjugated Annexin V was from BD Bioscience. Human thrombin was from Sigma-Aldrich. Human thrombin was from Sigma-Aldrich. Size standard fluorescent beads (0.22, 0.45, 0.88 and 1.34 µm) and AccuCount fluorescent particles (5.1 µm) were from SpheroTech.

Antibodies:

Fluorescein isothiocyanate (FITC)-conjugated anti-CD41a (GPaIIb), PE-conjugated anti-CD42b (GPIbα), PE-conjugated anti-CD62P, allophycocyanin (APC)-conjugated anti-BrdU (BrdU APC flow kit), APC-conjugated anti-CD34, PE-conjugated CD11b and APC-conjugated anti-CD235a antibodies were from BD Bioscience. Anti-active caspase-3 antibody (ab13847), anti-human β31 tubulin antibody (ab96008), anti-human vWF antibody (ab9378) and anti-serotonin antibody (ab66047) were all from Abcam. The secondary antibodies, Alexa Fluor® 488-conjugated anti-rabbit IgG antibody and anti-goat IgG antibody, were from Life Technologies. FITC-conjugated CD41 antibody for CD41$^+$-cell enrichment and platelet functionality assays was from Beckman Coulter.

Megakaryocytic Cultures:

Frozen G-SCF mobilized peripheral blood CD34$^+$ cells were obtained from the Fred Hutchinson Cancer Research Center. CD34$^+$ cells were cultured using the protocol previously described. Briefly, from day 0 (d0) to d5, cells were cultured in Iscove modified Dulbecco medium (IMDM, GlutaMax™; Life Technologies), pH 7.2, supplemented with 20% BIT9500 (Stemcell Technologies), 100 ng/mL rhTPO, 100 ng/mL rhSCF, 2.5 ng/mL rhIL-3, 10 ng/mL rhIL-6, 10 ng/mL rhIL-11 and 1 µg/mL human low density lipoprotein (hLDL), at 37° C. in fully humidified incubator under 5% $CO_2$ and 5% $O_2$. Then from d5 to d7, culture medium was changed to IMDM, pH 7.4, supplemented with 20% BIT9500, 100 ng/mL rhTPO, 100 ng/mL rhSCF, 10 ng/mL rhIL-3, 10 ng/mL rhIL-9, 10 ng/mL rhIL-11 and 1 µg/mL hLDL, and $O_2$ level was increased to 20%. At d7, CD61$^+$ cells (Mks) were enriched using anti-CD61 magnetic microbeads (Miltenyi Biotec) and LD magnetic columns (Miltenyi Biotec). After enrichment, Mks (CD41$^+$ purity >90%) were cultured in IMDM, pH 7.6, supplemented with 20% BIT9500, 100 ng/mL rhTPO, 100 ng/mL rhSCF, 1 µg/mL hLDL and 6.25 mM nicotinamide. From d8 to d12, CD41 and CD62P expression and concentration of microparticles (MPs) in cell culture were measured by flow cytometer (FACSAria II, BD Biosciences) using AccuCount fluorescent particles as internal control.

Shear-Stress Experiments: Exposure of Mk Cells to Shear Flow:

Rectangular flow slides (µ-Slide I$^{0.6}$ Luer, ibidi USA) were coated with 50 µg/mL vWF, and ca. 300,000 cultured Mks were seeded into each slide. Mks on slides were cultured overnight (21 hours) before being exposed to shear flow. Medium (IMDM supplemented with 10% BIT9500, 50 ng/mL TPO, 50 ng/mL rhSCF, 0.5 µg/mL hLDL and 6.25 mM nicotinamide) was perfused over Mks on slides by two syringe pumps (Dual NE-4000 pump; New Era Pump Systems) to achieve the desirable shear-stress level. For BrdU incorporation assays, the medium was supplemented with 10 µM BrdU (BD). During shear flow, some Mks were detached from the slide surface and released into the circulating medium. These are considered as non-adherent Mks. Adherent Mks were harvested for analysis using non-enzymatic cell dissociation buffer (Sigma-Aldrich). In some experiments, adherent Mks were fixed with 2% paraformaldehyde directly on slides and processed for immunofluorescence analysis. In some experiments, Mks were treated with caspase inhibitors, 10 µM z-VAD.fmk (Bachem) or 10 µM z-DEVD.fmk (Bachem) starting on d9. Inhibitor-treated Mks were seeded into flow slides at d9 or d11, were exposed to shear flow (2.5 dyn/cm$^2$ for 0.5 hour) in medium supplemented with the same inhibitor, and were harvested for PPT, PLP and CD41$^+$ microparticle counting.

DNA Synthesis Assay:

DNA synthesis was assessed using a BrdU APC flow kit (BD Bioscience). After exposure to shear flow for the indicated time, Mks were cultured for additional time period to a total 4 of hours with BrdU in the medium before harvesting for analysis. Cells from static cultures were treated the same way and served as control Annexin V Assay:

After shear flow application or static control, cells were harvested immediately and stained with FITC-anti-CD41a antibody and PE-Annexin V for flow-cytometric analysis.

Immunofluorescent Staining:

For β1 tubulin staining, cells were fixed and permeabilized using 1% glutaraldehyde and 0.1% Triton® X-100 (Sigma-Aldrich) in PHEM buffer (60 mM PIPES, 25 mM HEPES, 10 mM EGTA, 2 mM MgCl$_2$, pH6.9). Then, cells were quenched in 1~2 mg/mL sodium borohydride before blocking. For other staining, cells were fixed with PFA and permeabilized with Triton X-100. After blocking with BSA (Fisher Scientific) together with normal goat or donkey serum (MP Biomedicals), primary antibodies (active caspase-3, β1 tubulin, vWF or serotonin) or corresponding isotype controls were applied to cells overnight at 4° C., followed by incubation with the secondary antibody conjugated with Alexa Fluor® 488 at room temperature for 1 hour. F-actin and DNA were stained with Alexa Fluor® 568-phalloidin (Life Technologies) and TO-PRO®-3 (Life Technologies), respectively. Fluorescent images were collected via a multiphoton confocal microscope (Zeiss 510 NLO). Mean fluorescent intensity (MFI) of active caspase-3 and the average area for a single Mk were quantified using Velocity® Image Analysis Software (Perkin Elmer).

Isolation of PLPs:

Large cells were excluded from PLP preparations by centrifugation at 150×g for 10 minutes. PLPs were then pelleted by centrifugation at 1000×g for 10 minutes from the PLP-enriched supernatant. After one wash, PLPs were resuspended in Tyrode's buffer and used in platelet-stimulation assays. The number of PLPs and PPTs per slide was measured using a Multisizer™ 3 Coulter Counter (Beckman Coulter).

Platelet-Stimulation Assays: CD62P Exposure and Fibrinogen Binding:

These assays were carried out as described, whereby CD62P expression and fibrinogen binding were measured by flow cytometry.

Preparation of Human Platelet and Platelet-Derived Microparticles (PMPs):

Blood for isolation of human platelets was collected by venipuncture from adult human volunteers after providing written informed consent as approved by the Institutional Review Board at University of Delaware (IRB protocol #190471-3). Blood was collected into a 60-cc syringe containing ACD (trisodium citrate, 65 mM; citric acid, 70 mM; dextrose, 100 mM; pH 4.4) at a ratio of 1:6 parts ACD/blood. Anticoagulated blood was spun by centrifugation at 250×g and the supernatant containing platelet rich plasma (PRP) was then pelleted at 750×g (10 minutes), washed once in HEN buffer (10 mM HEPES, pH 6.5, 1 mM EDTA, 150 mM NaCl) containing 0.05 U/ml apyrase and platelets resuspended in HEPES-Tyrode's buffer (137 mM NaCl, 20 mM HEPES, 5.6 mM glucose, 1 g/l BSA, 1 mM MgCl2, 2.7 mM KCl, 3.3 mM NaH2PO4) at a concentration of 4×10$^8$ platelets/ml in HEPES-Tyrode's buffer containing 0.05 U/ml apyrase. 1 mM CaCl$_2$) was added to platelet before activation and platelets were activated by 2 U/mL human thrombin or 10 µM Calcium Ionophore (A23187, Sigma-Aldrich). The platelets were removed by centrifugation at 1000×g for 10 minutes and PMPs were harvested from supernatant washed two times using IMDM medium by ultracentrifugation at 25,000 rpm for 1 hour, 4° C. The concentration of PMPs was measured by flow cytometry using 1.34 µm-diameter microbeads.

ELISA Assay for TPO:

Protein lysates and supernatants from concentrated microparticle suspensions were analyzed using human TPO ELISA (PeproTech) according to manufacturer's protocol. The signal was read at 405 nm on a PerkinElmer Victor 3V multilabel counter.

Isolation and Characterization of MkMPs:

For both static cultures and cultures exposed to shear flow, Mk cells were removed from the culture medium by centrifugation (150×g for 10 minutes). Following that, PLPs were removed by centrifugation at 1000×g for 10 minutes. Particles were then washed twice in IMDM medium and were enriched for MkMPs by ultracentrifugation (25,000 rpm for 1 hour at 4° C.; Beckman Coulter Optima Max Ultracentrifuge). CD41, CD42b and CD62P expression was examined by flow cytometry. Concentrations of MkMPs (and of PMPs and Mks) were measured by flow cytometry using 1.34 µm microbeads (Sphero Tech) as standard. For some experiments, MkMPs in supernatant were incubated with 1 U/mL RNase A/T1 cocktail (Life Technologies) or 10 U/mL RNase ONE™ (Promega) for 1 hour at 37° C. before enrichment.

Human Umbilical Vascular Endothelial Cells (HUVECs), Mesenchymal Stem Cells (MSCs) and Granulocytic Cultures:

Primary HUVECs were obtained from ATCC and cultured according to ATCC recommendation (growth medium from ATCC: vascular cell basal medium supplemented with endothelial cell growth kit-VEGF). Human MSCs were obtained from Lonza and cultured according to Lonza recommendation (growth medium: mesenchymal stem cell basal medium supplemented with MSCGM™ Single-Quots™). Human granulocytes were differentiated from human CD34$^+$ cells as previously described. Human long-term medium (HLTM) was prepared by supplementing McCoy's 5A medium with 12.5% heat-inactivated (57° C. for 30 minutes) fetal bovine serum (Hyclone), 12.5% heat-inactivated horse serum, 1 mM sodium pyruvate, 2 mM L-glutamine, 1% minimal essential medium (MEM) essential amino acid solution (Life Technologies), 1% MEM nonessential amino acid solution (Life Technologies), 1% MEM vitamin solution (Life Technologies), 100 mM monothioglycerol, 10 mM HEPES, and 50 mg/mL gentamycin sulfate. CD34$^+$ cells were cultured in HLTM supplemented with 50 ng/mL rhSCF, 10 ng/mL rhIL-3, rhIL-6 and rhG-CSF (supplement fresh rhG-CSF every 2 days due to degradation) in fully humidified incubator under 5% CO$_2$ and 5% O$_2$. At d7 of cell culture, CD15$^+$ cells were enriched using MS column and CD15 microbeads (Miltenyi Biotec).

Mk Ploidy Analysis:

Cells from MkMP coculture were stained with FITC anti-CD41 antibody before fixation by 0.5% paraformaldehyde (Electron Microscopy Sciences) and permeabilization by 70% methanol/$H_2O$. After RNA was degraded by RNase A (Life Technologies), DNA was stained with 100 g/mL propidium iodide. Analyses of CD41 expression level, cell ploidy and numbers were performed on flow cytometry using AccuCount fluorescent particles as internal control.

MkMP Binding and Uptake Analysis:

MkMPs were stained with 20 μM CFDA-SE (Life Technologies) for 20 minutes at 37° C. and washed three times in IMDM medium. Then MkMPs were cocultured with HPCs from d3 Mk culture at concentration of 30 MkMPs/cell for indicated time before analysis. For the first hour, the coculture medium was 50 μL IMDM and after that coculture was diluted in IMDM supplemented with 5% BIT9500, 50 ng/mL rhSCF and 1% pen strep (Life Technologies). Flow cytometry was used to measure binding of MkMPs to cells. In some experiments, after 3 hours, images of coculture were collected via confocal microscope (Zeiss 5 μLIVE DUO Highspeed/Spectral Confocal, Bioimaging Center, Delaware Biotechnology Institute).

Transmission Electron Microscopy (TEM):

Cells from coculture were fixed in 2% glutaraldehyde and 2% paraformaldehyde in 0.2 cacodylate buffer overnight at 4° C., washed, postfixed within 2% osmium tetroxide for 1 hour at room temperature, followed by 4 washes in $H_2O$. The samples were then stained en bloc overnight at 4° C. with 1% uranyl acetate. After dehydrated in a series of ascending acetone solutions, samples were infiltrated within n-BGE and then Quetol-NSA resin. Samples were then embed in labeled BEEM capsules and polymerized at 60° C. for 24-48 hours. Ultrathin sections were prepared using a Reichert Jung Ultracut E ultramicrotome, and were collected onto 200 mesh formvar/carbon coated copper grids. Grids were stained with 2% methanolic uranyl acetate and Reynolds' lead citrate. Transmission Electron Microscopy was performed on Zeiss Libra 120 Transmission Electron Microscope and images were acquired using a Gatan Ultrascan 1000 CCD.

Scanning Electron Microscopy (SEM):

The d3 HPCs from Mk culture were incubated with MkMPs (10 MPs/cell) in 100 μL medium for 2 or 4 hours. Then the coculture was let spread on circle coverslip coated with 1 μg/mL human fibronectin for another hour. 2% EM grade glutaraldehyde/IMDM medium was added to coverslips to fix the cells for at least 1 hour at room temperature or overnight at 4° C. Then the samples were washed with PBS and postfixed for 1.5 hours in 1% $OsO_4$ in $H_2O$ at room temperature. After rinsed with $H_2O$, the samples were dehydrated in a series of ascending ethanol concentrations for 10 minutes in each solution. After critical-point drying by Autosamdri-815B Critical Point Dryer (Tousimis), the samples were sputter-coated with gold using a Bench Top Turbo III Sputter Coater (Denton Vacuum). The electron images were collected via Hitachi S4700 Field-Emission Scanning Electron Microscope (Hitachi) at a working distance of 8.5-10.5 mm and voltage of 3.0 kV.

Statistical Analysis:

Paired Student t test of all data was performed by Minitab 16 (Minitab). Statistical significance was defined as $P<0.05$.

Figure 2:
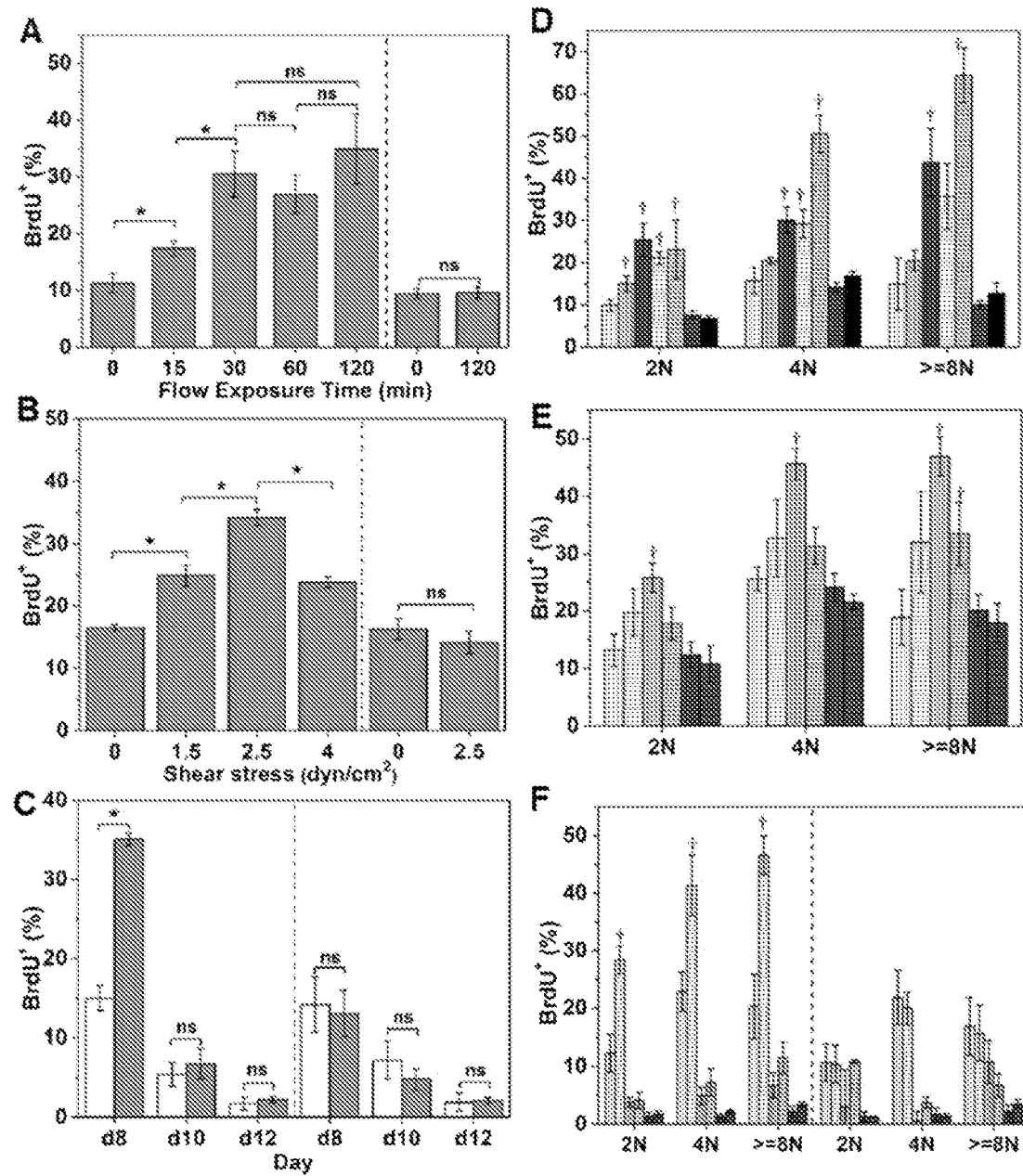
FIG. 2. Shear stress enhances DNA synthesis of immature Mks. The BrdU$^+$ percentage of all adherent and non-adherent Mks (A-C) or Mks with different ploidy classes (2N, 4N and >=8N) (D-F) upon exposure to various shear-stress conditions. After shear-flow application, Mks were cultured in the presence of BrdU for a total of 4 hours. Cells were then harvested for CD41 and PI (DNA) staining and analyzed by flow cytometry. (A, D) At d8, Mks were exposed to shear stress at level of 2.5 dyn/cm$^2$ for 0 (static control), 15, 30, 60, and 120 minutes. (B, E) At d8, Mks were exposed to shear stress at 0 (static control), 1.5, 2.5 and 4.0 dyn/cm$^2$ for 30 minutes. (C, F) At d8, d10, and d12, Mks were exposed to 2.5 dyn/cm$^2$ for 30 minutes. (A, B, C, F) Adherent Mks are shown on the left side and non-adherent cells are shown on the right side of charts. (C) The white bars represent static condition and the grey bars represent flow condition. (D) The white bars filled with vertical lines represents adherent Mks with 0 minute of flow exposure; the light grey bars filled with vertical lines represents adherent Mks with 15 minutes of flow exposure; the dark grey bars filled with vertical lines represents adherent Mks with 30 minutes of flow exposure; the white bars filled with horizontal lines represents adherent Mks with 60 minutes of flow exposure; the light grey bars filled with horizontal lines represents adherent Mks with 120 minutes of flow exposure; the dark grey bars filled with horizontal lines represents non-adherent Mks with 0 minute of flow exposure; the black bars represents non-adherent Mks with 120 minutes of flow exposure. (E) the white bar filled with vertical lines represent adherent Mks exposed to shear stress at level of 0 dyn/cm$^2$; the white bar filled with horizontal lines represent adherent Mks exposed to shear stress at level of 1.5 dyn/cm$^2$; the light grey bar filled with vertical lines represent adherent Mks exposed to shear stress at level of 2.5 dyn/cm$^2$; the light grey bar filled with horizontal lines represent adherent Mks exposed to shear stress at level of 4.0 dyn/cm$^2$; the dark grey bar filled with vertical lines represent non-adherent Mks exposed to shear stress at level of 0 dyn/cm$^2$; the dark grey bar filled with horizontal lines represent non-adherent Mks exposed to shear stress at level of 2.5 dyn/cm$^2$; (F) The bars filled with vertical lines represent static condition and the bars filled with horizontal lines represent flow condition; the white bars represent Mks at d8; the light grey bars represent Mks at d10; the dark grey bars represent Mks at d12. Error bars indicate standard error of mean (SEM) of 3 biological replicates. *P<0.05; †, P<0.05 compared to corresponding static control; ns, not significant.

Example 1. Shear Flow Promotes DNA Synthesis and Accelerates the Polyploidization of Mks in a Largely Dose and Maturation-Stage Dependent Way Mk cells engage endomitosis as they mature and become polyploid. We hypothesized that biomechanical forces, such as physiological shear forces, would impact DNA synthesis. To investigate this hypothesis, Mk cells from d7 of culture were seeded onto vWF-coated slides and cultured overnight before exposure to shear flow using perfusion with medium containing 10 μM BrdU. We employed a validated perfusion system (FIG. 1) designed to expose cells to defined shear stress. For our experiments, we used shear in the physiological range of 1.3-4.1 $dyn/cm^2$. First, we exposed d8 Mk cells to 2.5 $dyn/cm^2$ for 0 (static control), 15, 30, 60 or 120 minutes. Exposure to shear flow increased DNA synthesis of Mk cells by up to 3-fold, and the increase was exposure-time dependent (FIG. 2A). Mks responded to shear stress quickly, certainly within 15 minutes, but after 30 minutes, no further increase in DNA synthesis was observed. This is physiologically relevant. It has been reported that, in vivo, the time needed for trans-sinusoidal migration of murine Mk fragments into the blood stream is about 30 minutes [1]. In subsequent experiments, an exposure time of 30 minutes was used to investigate the impact of shear-stress level on Mks. Low levels of shear stress (1.5 $dyn/cm^2$) enhanced DNA synthesis of d8 Mks by 51% compared to static conditions (FIG. 2B). Exposure to 2.5 $dyn/cm^2$ increased DNA synthesis further by 37% over that of 1.5 $dyn/cm^2$, or 107% over static control (FIG. 2B). However, at 4.0 $dyn/cm^2$ (near the upper limit of the physiological range of shear stress in the bone marrow of mammals; see Refs. [1,9]), DNA synthesis was similar to that at 1.5 $dyn/cm^2$.

To investigate if shear flow differentially affects DNA synthesis at different differentiation stages, Mks at d8, d10 and d12 were exposed to 2.5 $dyn/cm^2$ for 30 minutes. Our data (FIG. 2C) show that exposure to shear flow results in increased DNA synthesis only of d8 Mk cells. Mks at d10 or d12 are more mature, thus displaying much lower DNA synthesis compared to d8 cells. We also examined if shear affects Mks of different ploidy classes (2N, 4N, >=8N Mks) differently. DNA synthesis of each ploidy class showed trends similar to those of the total Mk population (FIGS. 2D-F). However, DNA synthesis of Mks with 4N and higher ploidy classes increased further when 2.5 $dyn/cm^2$ was applied for 120 minutes (FIG. 2D). These data suggest that even short exposure to circulatory shear promotes the maturation of less mature d8 Mk cells as assessed by accelerated DNA synthesis of all ploidy classes but also by enhanced polyploidization under some flow conditions.

We also examined the impact of biomechanical forces on non-adherent cells. In contrast to adherent Mk cells, DNA synthesis of non-adherent Mk cells in these experiments was not affected compared to static conditions (FIGS. 2A-C).

Figure 3:
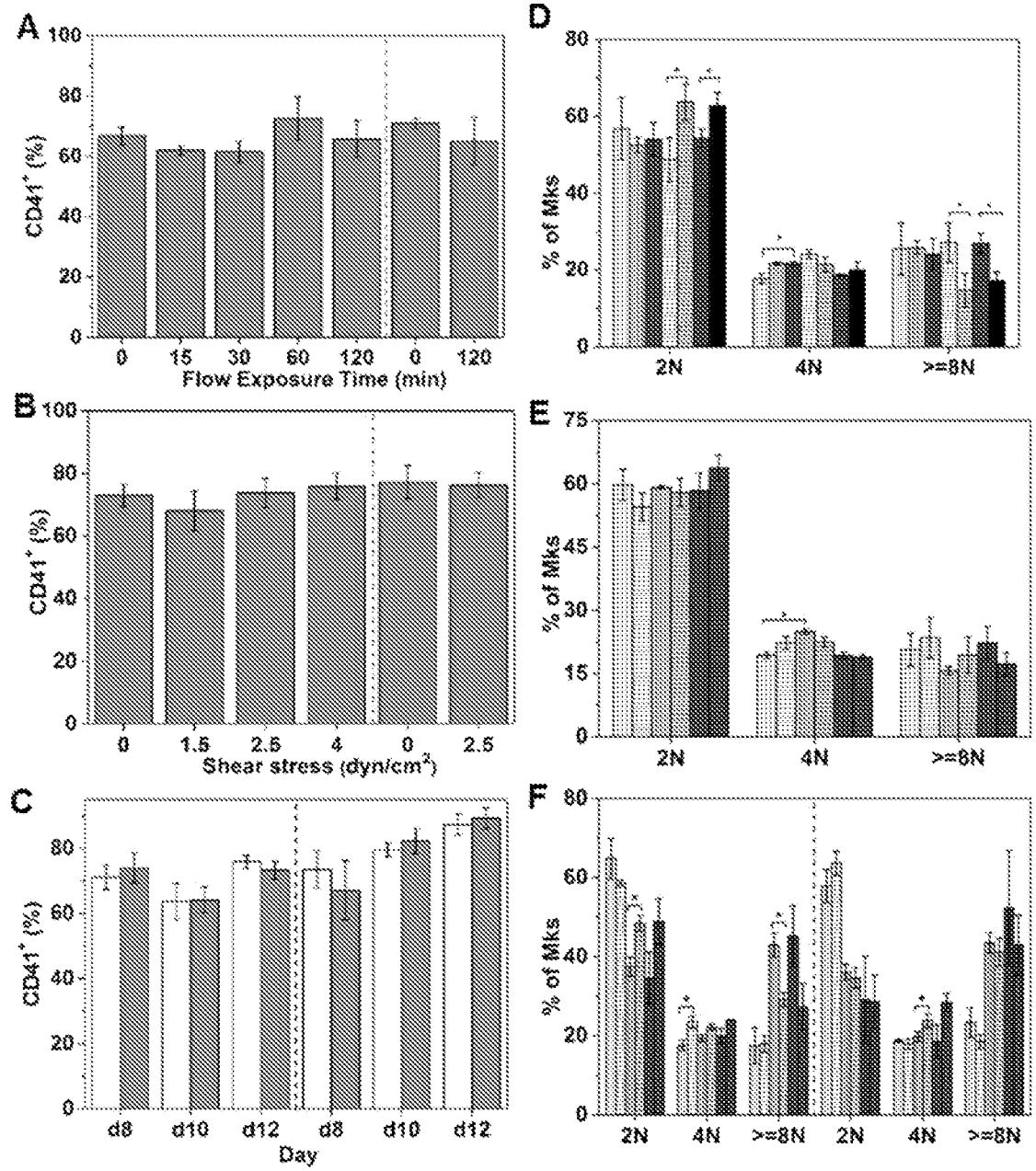
FIG. 3. CD41+% and ploidy distribution of Mks exposed to shear stress versus static condition. (A-C) % CD41+ of cells. (D-F) ploid distribution of Mk cells. (A, D) At d8, Mks were exposed to shear stress at level of 2.5 dyn/cm2 for various times: 0, 15, 30, 60, and 120 minutes. (B, E) At d8, Mks were exposed to shear stress at various levels: 0, 1.5, 2.5 and 4.0 dyn/cm2 for 30 minutes. (C, F) At d8, d10, and d12, Mks were exposed to shear stress at level of 2.5 dyn/cm2 for 30 minutes. (A, B, C, F) Adherent Mks are shown on the left side and non-adherent cells are shown on the right side of charts. (C) The white bars represent static condition and the grey bars represent flow condition. (D) The white bar filled with vertical lines represents adherent Mks with 0 minute of flow exposure; the light grey bar filled with vertical lines represents adherent Mks with 15 minutes of flow exposure; the dark grey bar filled with vertical lines represents adherent Mks with 30 minutes of flow exposure; the white bar filled with horizontal lines represents adherent Mks with 60 minutes of flow exposure; the light grey bar filled with horizontal lines represents adherent Mks with 120 minutes of flow exposure; the dark grey bar filled with horizontal lines represents non-adherent Mks with 0 minute of flow exposure; the black bar represents non-adherent Mks with 120 minutes of flow exposure. (E) The white bars filled with vertical lines represent adherent Mks exposed to shear stress at level of 0 dyn/cm$^2$; the white bars filled with horizontal lines represent adherent Mks exposed to shear stress at level of 1.5 dyn/cm$^2$; the light grey bars filled with vertical lines represent adherent Mks exposed to shear stress at level of 2.5 dyn/cm$^2$; the light grey bars filled with horizontal lines represent adherent Mks exposed to shear stress at level of 4.0 dyn/cm$^2$; the dark grey bars filled with vertical lines represent non-adherent Mks exposed to shear stress at level of 0 dyn/cm$^2$; the dark grey bars filled with horizontal lines represent non-adherent Mks exposed to shear stress at level of 2.5 dyn/cm$^2$; (F) The bars filled with vertical lines represent static condition and the bars filled with horizontal lines represent flow condition; the white bars represent Mks at d8; the light grey bars represent Mks at d10; the dark grey bars represent Mks at d12. Error bars indicate standard error of mean (SEM) of 3 biological replicates. *$P<0.05$; $P<0.05$ compared to corresponding static control; ns, not significant.

Could the effect of shear stress on DNA synthesis be due to differential retention of adherent Mk cells because adherent Mks cells were more active in synthesizing DNA? Our data suggest that this is not the case. Indeed, the % $CD41^+$ cells and ploidy distribution among adherent Mks under various (stress level and duration) flow conditions and static conditions were similar (FIG. 3). In addition, we observed decreased DNA synthesis after the shear stress level was increased from 2.5 $dyn/cm^2$ to 4 $dyn/cm^2$ (FIG. 2B), and finally, DNA synthesis of Mks at d10 and d12 was not accelerated by shear stress.

We also found that Mk cells respond to higher shear stresses (up t0 400 $dyn/cm^2$, but more likely up to 100 $dyn/cm^2$) such as those encountered in the lung vasculature and systemic blood circulation (see Supplemental material of ref. [9]). Mk cells are trapped in the lung vasculature where they experience higher shear and normal stresses than in the bone marrow. Mk cells are also exposed to variable (in magnitude and frequency) shear and normal stresses, from both laminar and turbulent flows (this laminar and turbulent shear and other stresses) in the bone marrow and in systemic blood circulation due to the pulsatile blood flow, different blood vessel diameters and due to squeezing through blood-vessel endothelial cells (see Refs [1, 9] and Supplemental material of ref. [9]). Shear stresses can range from 0.1 to 100 dyn/cm2. Frequency of stress application can range from a few seconds (10, 20, 30, 60, 120 seconds to a few minutes, 1-10 minutes) depending on location in the blood and lung vasculatures and the trapping of Mk cells between other cells. All such biomechanical stresses of variable magnitude and frequency can stimulate Mk cells and can lead to increased DNA synthesis and the formation of various particles derived from Mk cells as described in the examples below.

Shear flow is a flow of fluid in a channel that creates a shear stress on the walls of the channel or on the surfaces of objects (such as cells or particles) in the flow channel. Shear stress, here due to fluid flow, is a mechanical stress that arises in a flow field in a channel or around an object (such as a cell or particle) in the flow field due to the changing fluid velocity in the channel in any cross section of the channel or for the case of flow around an object due to the changing velocity in the area of the flow field near the object. The shear stress is tangent to the fluid element surface. The shear stress is highest on the wall of the channel where the velocity changes the fastest, as in this case the cells are grown. A shear stress is also the highest near the surface of an object in a flow field. In a flow, the normal stress is perpendicular to the surface of the fluid element in a flow field. A laminar shear stress arises in a laminar fluid flow, which is the fluid flow where the fluid flows in parallel thin layers, with no disruption between the thin layers. Turbulent stresses arise in the complex fluid patterns of turbulent fluid flow, in which there are eddies created in the flow that create a chaotic pattern of fluid motion and where, in contrast to laminar flow, the fluid does not flow in orderly parallel thin layers.

Figure 4:
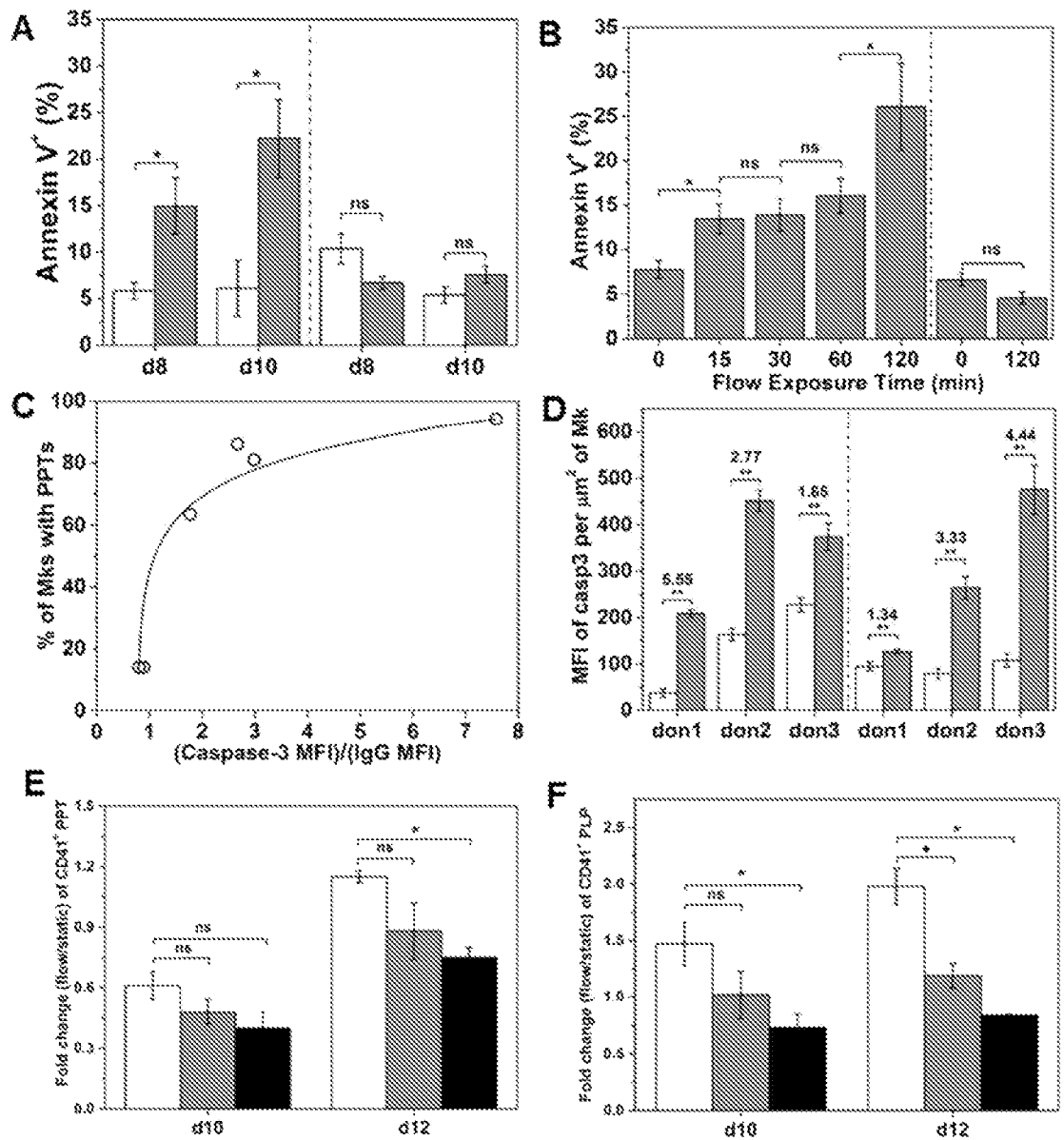
FIG. 4. Shear stress promotes phosphatidylserine (PS) externalization and caspase-3 activation, the early and late events of apoptosis. Caspase-3 is involved in shear-stress enhanced PPTs and PLPs formation. (A) Percent of Annexin V$^+$ Mks at d8 and d10 Mks after shear-flow application at 1 dyn/cm$^2$ for 2 hours versus static control. Adherent (left side) and non-adherent (right side) Mks were analyzed separately. The white bars represent Mks under static condition and the grey bar represents Mks under flow condition. (B) Percent of Annexin V$^+$d10 Mks exposed to 2.5 dyn/cm$^2$ for 0 (static control), 15, 30, 60, or 120 minutes. Adherent (left side) and non-adherent (right side) Mks were analyzed separately. (C) Correlation between caspase-3 activation and proplatelet (PPT) formation of Mks under static culture conditions. X-axis: caspase-3 activation level defined as the ratio of mean fluorescence intensity (MFI) of active caspase-3 over IgG control. Y-axis: percent of Mks bearing PPTs. (D) MFI of active caspase-3 per μm$^2$ of adherent d10 (left side) and d12 (right side) Mks from different donors (don) after shear-flow exposure at 1.0 dyn/cm$^2$ for 2 hours versus static control. The white bars represent Mks under static condition and the grey bars represent Mks under flow condition. The ratio of MFI of caspase-3 of Mks under shear-flow conditions over static control is indicated above the bars. Under shear flow, MFI values for caspase-3 activation were well above the MFI for isotype control, so there was no need to correct for isotype control. (E, F) At d10 and d12, DMSO (vehicle control, white bars) or z-VAD.fmk (pan-caspase inhibitor, grey bars) or z-DEVD.fmk (caspase-3 inhibitor, black bars) treated Mks were exposed to shear flow at 2.5 dyn/cm$^2$ for 0.5 hour. After shear-flow exposure, PPTs and PLPs were harvested and counted. The number of PPTs (E) or PLPs (F) from one slide of Mks exposed to shear flow was normalized by number of PPTs or PLPs on a slide under static conditions, and the resulting ratios are plotted. Error bars indicate SEM of 3~4 biological replicates in panel (A, B, E and F) and 6~10 different images in panel (D). **$P<0.01$; *$P<0.05$; ns, not significant.

Example 2. Shear Stress Promotes Phosphatidylserine (PS) Surface Exposure on Maturing Mk Cells As an early mark of apoptosis, previous studies in our lab and other labs have shown that PS becomes exposed on the extracellular side of the Mk membrane when HPSCs (both human and murine) were differentiated into Mks. In this study, to differentiate human CD34$^+$ cells into Mks, we used a new protocol that gives rise to functional PLPs in vitro. Using flow cytometry and microscopic analyses, we confirmed that PS is also exposed on the surface of maturing (>d8) Mks generated by this protocol (data not shown). To investigate if shear promotes PS externalization, fluid flow at 1 dyn/cm$^2$ was applied to d8 and d10 Mks for 2 hours. Cells were harvested immediately after the shear-flow application for analysis. Shear resulted in a significantly increased fraction (by ca. 160% and 260% at d8 and d10, respectively) of adherent Mks that are Annexin V$^+$, but not so for non-adherent Mks (FIG. 4A). We also examined the impact of shear exposure time on PS externalization by exposing d10 cells to 2.5 dyn/cm$^2$ for 0 (static condition), 15, 30, 60 and 120 minutes. PS externalization responded quickly to shear stress: the fraction of adherent Mk cells that became Annexin V$^+$ increased by more than 70% after 15 minutes of exposure to shear flow (FIG. 4B). PS externalization plateaued for exposure times between 15 and 60 minutes, but increased further at 120 minutes (FIG. 4B). Shear flow did not affect PS externalization of non-adherent Mks (p>0.10) (data for 0 and 120 minutes are only shown; FIG. 4B).

Figure 5:
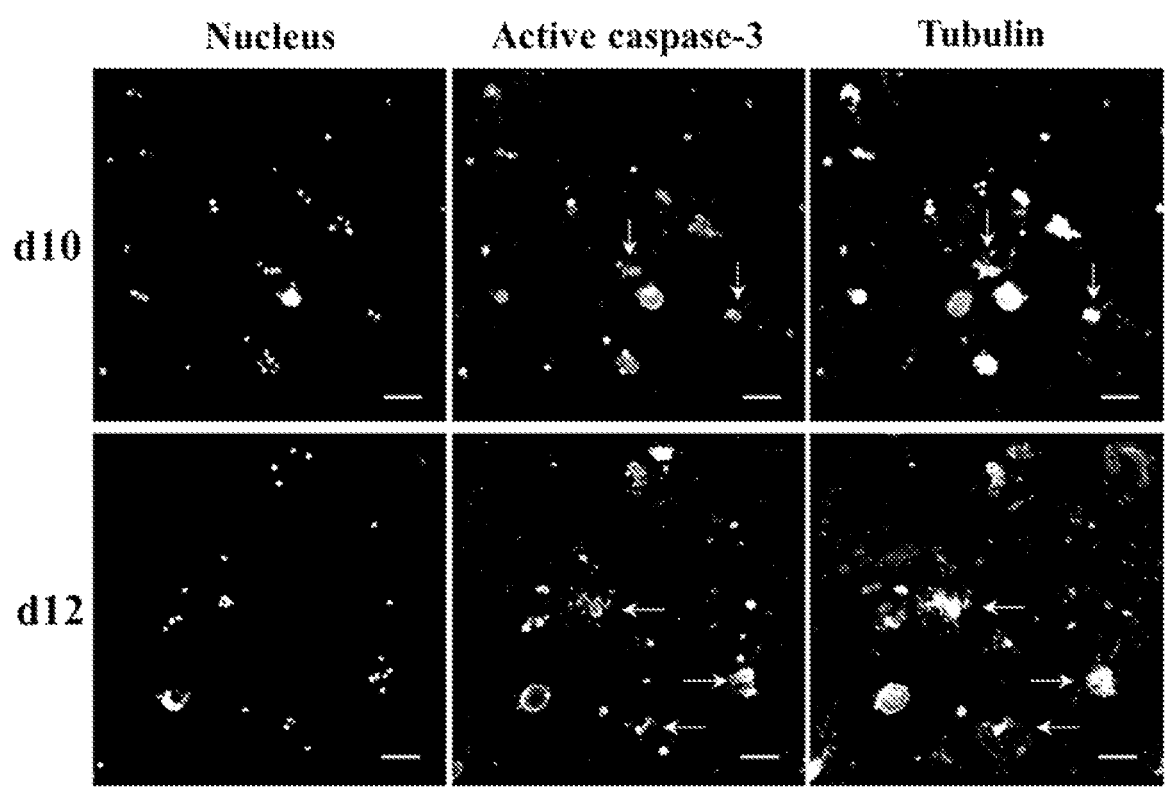
FIG. 5. Caspase-3 is activated during Mk differentiation under static culture conditions. Representative image showing that both round Mks without PPTs and Mks with PPTs (arrow) are positive of active caspase-3 at d10 and d12 under static culture conditions. The scale bar represents 50 Gm.

Example 3. Caspase-3 Activation in Maturing Mk Cells is Accelerated by Exposure to Shear Flow It has been shown that activation of caspase-3 and 9 is required for PPT formation. Here we wanted to investigate if shear stress affects caspase-3 activation in Mks. We chose caspase-3 as a marker of late apoptosis to complement our Annexin V studies above, which pertain to early apoptotic events. First, we confirmed that caspase-3 in indeed activated during in vitro Mk maturation with our culture protocol. Caspase-3 was activated at d10 and d12 when Mks projected PPTs under our culture protocol; active caspase-3 accumulated largely around the nucleus, but PPTs did not stain for active caspase-3 (FIG. 5). We also observed a correlation between the activation level of caspase-3 in Mks (represented as the ratio of MFI of active caspase-3 over isotype control) and PPT formation (FIG. 4C), which is consistent with previous studies discussed above. Next, we investigated if shear stress enhances caspase-3 activation in maturing Mks, notably at d10 and d12. Exposure of Mks for 2 hours to 1 dyn/cm$^2$ enhanced caspase-3 activation both at d10 and d12 (FIG. 4D) by 1.7 to 5.6 fold depending on the donor and day. Since, as discussed, caspase-3 activation is necessary for PPT formation, one mechanism by which shear stress may promote PPT formation (see below) is by enhancing caspase-3 activation. To investigate this hypothesis, Mks were treated with 10 µM z-VAD.fmk (pan-caspase inhibitor) or z-DEVD.fmk (caspase-3 inhibitor) and were then exposed to shear flow. After flow application, PLPs (d=1-3 µm) and PPTs (d=3-10 µm) were harvested and counted. The effect of shear stress on particle generation was assessed using the ratio of PLP or PPT number from one slide of Mks under flow conditions over that under static conditions. At d10, z-VAD.fmk had no statistically significant effect on the PLP and PPT ratios, and z-DEVD.fmk decreased only the PPT ratio (FIGS. 4E and 4F). However, at d12, both of z-VAD.fmk and z-DEVD.fmk decreased both the PPT and PLP ratios (FIGS. 4E and 4F). These data suggest that at the d10 early maturation stage, at which time Mks were starting to project PPTs and very few PLPs were formed, the caspase-3 inhibitor inhibited the effect of shear stress on PPT generation but not on PLP generation. At d12 when Mks produced more PPTs and stared to form a significant number of PLPs, the effect of shear on PPT and PLP generation was attenuated by caspase inhibitors. These data suggest that caspase-3 activation plays a role in the mechanism by which shear stress enhances PPT and PLP formation.

Figure 6:
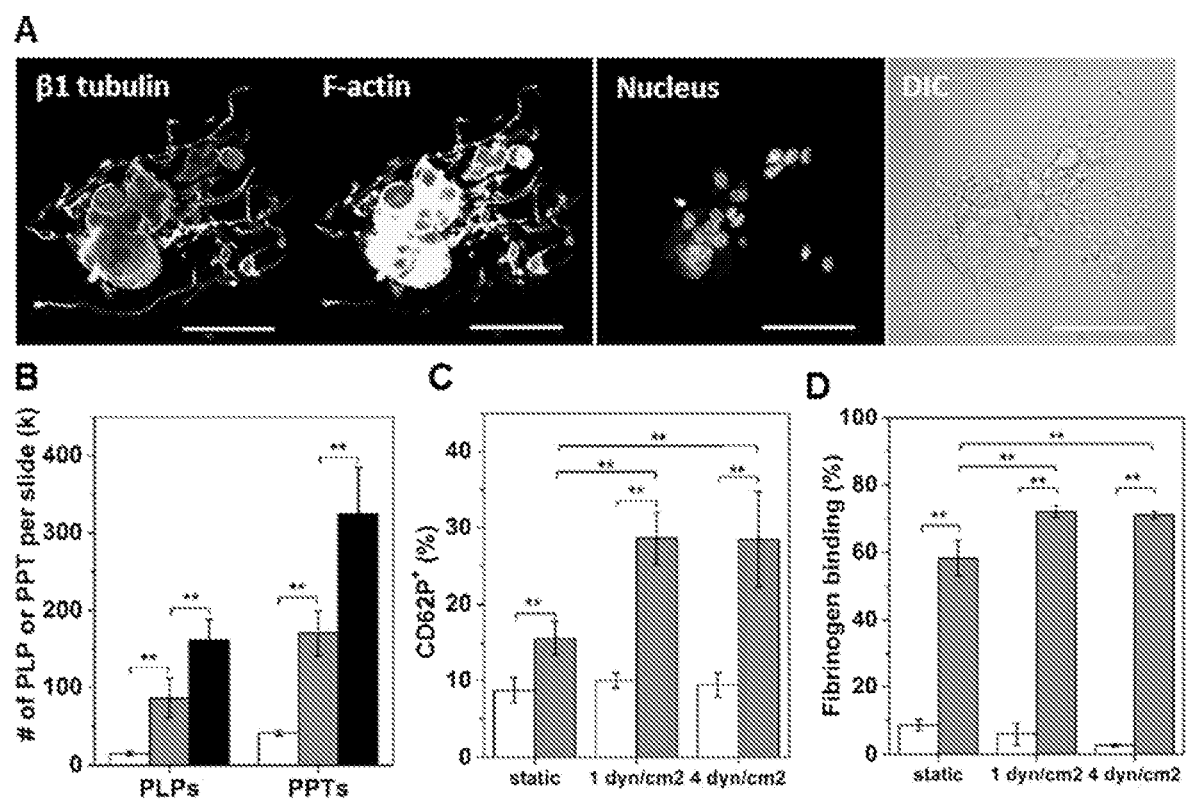
FIG. 6. Shear stress enhances the production of pre-/proplatelets (PPTs) and platelet-like particle (PLP). PLPs generated under shear flow display enhanced in vitro functional activity. (A) A mature and polyploid Mk displays extensive PPTs in static culture at d12. Scale bar: 50 m. (B-D) Mks at d12 were exposed to a shear flow at 1 dyn/cm$^2$ for 2 hours or 4.0 dyn/cm$^2$ for 0.5 hour. Both adherent and non-adherent cell fragments were analyzed post shear exposure. (B) Numbers of PLPs and PPTs per slide post shear exposure versus static control; the white bars represent samples from static condition; the grey bars represent samples from flow condition with shear stress at 1 dyn/cm$^2$ for 2 hours; the black bars represent samples from flow condition with shear stress at 4 dyn/cm$^2$ for 0.5 hour. Two functionality assays, CD62P exposure (C) and fibrinogen binding (D), were performed on the harvested PLPs, demonstrate enhanced activity for PLPs generated under shear flow. (C, D) The white bars represent PLPs without thrombin stimulation and the grey bars represent PLPs stimulated with 3 U/mL thrombin. Error bars in panel (B-D) indicate SEM of 3~4 biological replicates. *$P<0.05$; **$P<0.01$.

Example 4. Shear Stress Enhances the Generation of Functional Platelet-Like Particles (PLPs) as Well PLP Activity Here we aimed to investigate and quantify the effect of shear stress on the generation of Mk fragments with platelet-like properties at d12 when Mks had extensive PPTs (FIG. 6A). After a 2-hour exposure of adherent Mks to 1 dyn/cm$^2$, 5.8 times more PLPs were formed compared to static conditions, while exposure to 4 dyn/cm$^2$ for 0.5 hour yielded even more PLPs (ca. 10.8-fold higher than static control; FIG. 6B). Moreover, the number of PPTs increased by 4.1 and 7.9 fold after 2 hours of exposure to shear flow at 1 dyn/cm$^2$ and 0.5 hour of exposure to 4 dyn/cm$^2$, respectively (FIG. 6B). These data show that, in vitro at least, exposure to physiological levels of shear results in a dramatic increase in both PLP and PPT formation from mature Mks. These data could not have been anticipated by the findings of the study in ref. [4], and constitute a potent way for generating PLPs for transplantation application, which we claim in this application.

Next, we examined the impact of shear flow on the functionality of the generated PLPs. Is it possible that the fast generation of PLPs under shear flow results in lesser quality of PLPs, or perhaps the opposite? To do so, we employed two platelet-function assays, CD62P exposure and fibrinogen binding assays, both using the physiological activator: human thrombin. For PLPs generated from Mks under 1 dyn/cm$^2$ for 2 hours, the fraction of PLPs expressing CD62P increased by almost 3-fold (from 10% to 29%) upon thrombin activation, while for PLPs generated from Mk cells under static conditions this fraction increased by 1.8-fold (from 9% to 16%; FIG. 6C). After activation with thrombin, the % of PLPs generated from Mks under shear flow (1 dyn/cm$^2$ for 2 hours) that bind fibrinogen increased by 12-fold (from 6% to 72%), while that of PLPs from static culture increased by ca. 6.5-fold (from 9% to 58%; FIG. 6D). The quality of PLPs generated under 0.5-hour exposure to higher shear (4 dyn/cm$^2$) was similar to PLPs generated under a 2-hour exposure to 1 dyn/cm$^2$ (FIGS. 6C and 6D). Taken together, these data suggest that PLPs produced from Mks upon exposure to shear flow have better functionality than PLPs generated under static conditions. To sum, exposure to shear, even briefly, results in dramatic increases in both the number and quality of PLPs when compared to static controls. This finding is supporting the claim we make to the effect that shear and generally biomechanical forces when used for the generation of PLPs and PPTs and thus for the in vitro production of platelets from cultured Mk cells will produce superior PLPs, PPTs and platelets.

Figure 7:
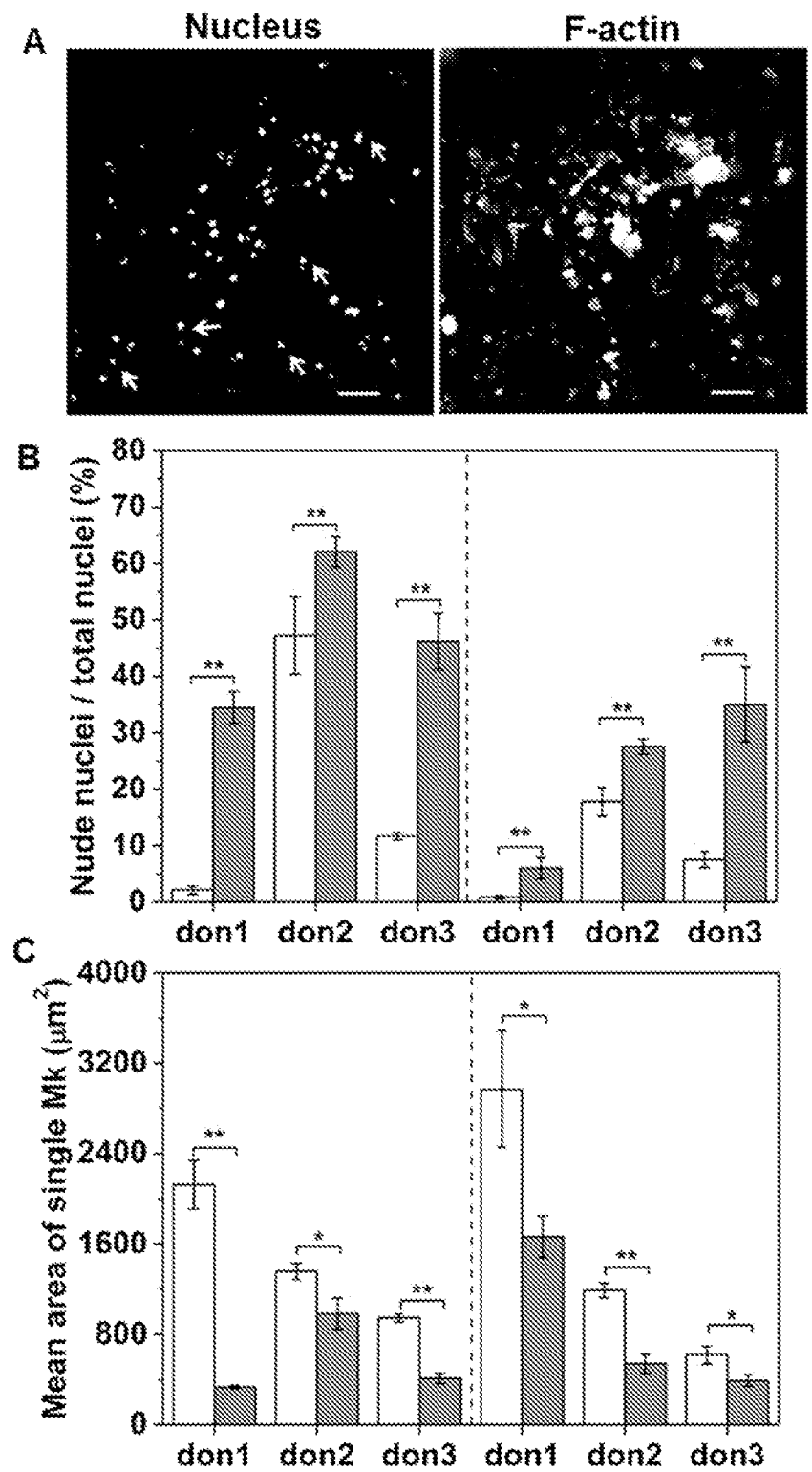
FIG. 7. Fragmentation of Mks by shear stress. (A) A representative fluorescent image of nude nuclei (indicated by white arrow) on slides of cultured Mk cells. The scale bar indicates 50 μm. (B, C) Mks generated from culture of CD34$^+$ cells from different donors (don) were exposed to shear flow at 1 dyn/cm$^2$ for 2 hours at d10 (left side) and d12 (right side) and were then stained with phalloidin (F-actin) and propidium iodide (DNA) for analysis. The percent of nude nuclei of the total number of nuclei (B) and the mean area (μm$^2$) of a single Mk (C) were measured from fluorescent images. (B, C) The white bars represent samples from static condition and the grey bars represent samples from flow condition. Error bars indicate SEM of 6 to 10 different images. *$P<0.05$; **$P<0.01$.

We also quantified the Mk-fragmentation outcomes aiming to illuminate and support the data of FIG. 6B. As expected, we observed a large number of nude nuclei (FIG. 7A) remaining on the slides after exposure to shear flow at 1.0 dyn/cm$^2$ for 2 hours. The morphology of these nuclei was round and their size similar to nuclei in intact cells, thus indicating that these were not apoptotic bodies. Staining for F-actin suggested that there was no cell cytoplasm attached to these nuclei. We quantified the fraction of nude nuclei over the total number of nuclei in each image. Compared to slides from static cultures, the fraction of nude nuclei was higher on the slides after shear flow both at d10 and d12 (FIG. 7B). In addition, we found that the mean surface area of single, intact Mks after exposure to shear flow was significantly smaller than that of Mks under static conditions (FIG. 7C), which shows that shear forces selectively fragment larger, more mature Mk cells. There are no prior quantitative studies on Mk-cell fragmentation under shear flow for the generation of PLPs, PPTs, platelets and MkMPs.

Example 5. Shear Stress Dramatically Enhances the Generation of Mk-Derived Microparticles (MkMPs)

Figure 8:
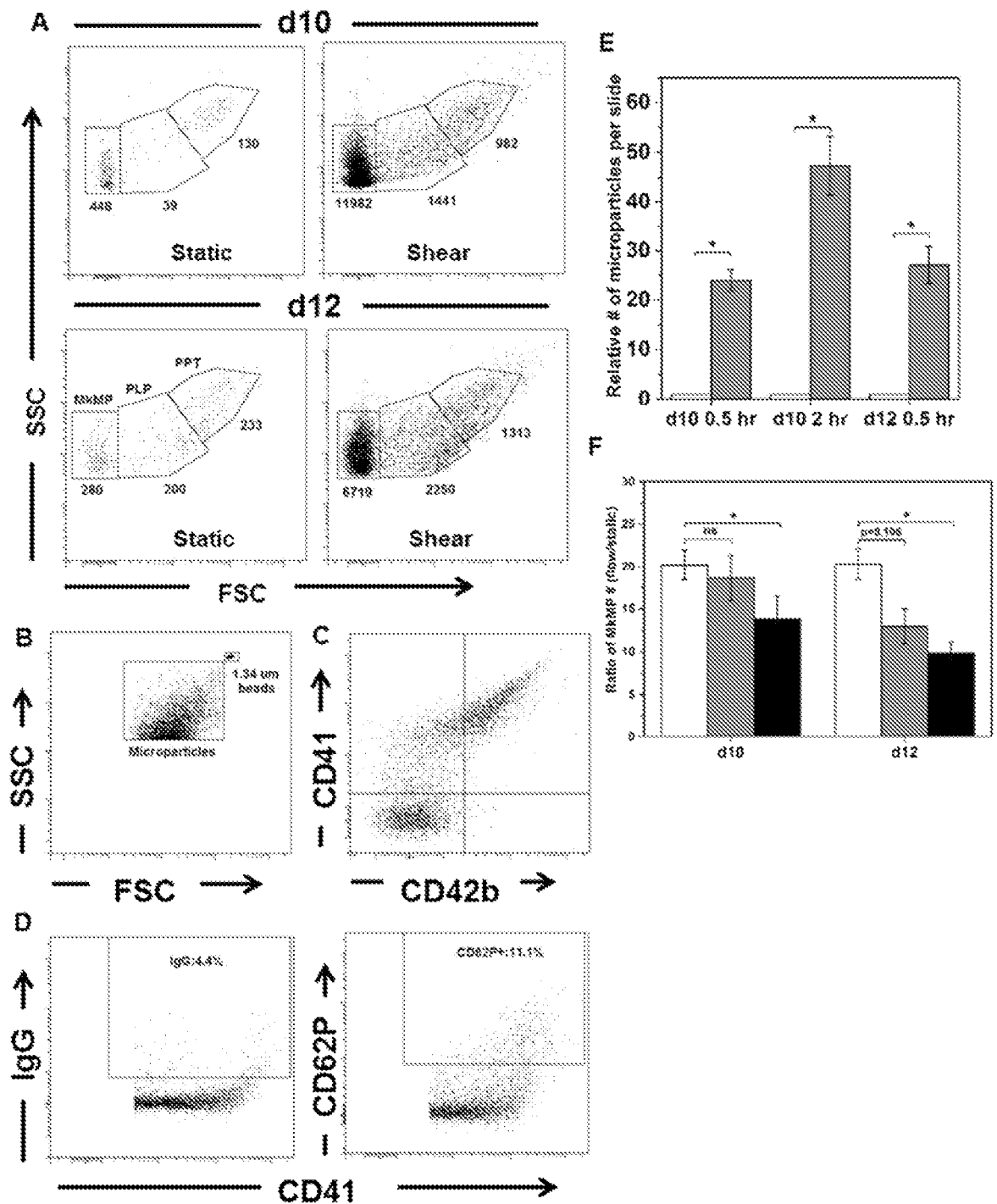
FIG. 8. Shear stress exposure results in dramatically enhanced generation of MkMPs through activation of caspase-3. (A) d10 and d12 Mks were exposed to medium flow at a shear stress of 2.5 dyn/cm$^2$ for 0.5 hour. Whole cells were removed and the same amount of samples, as assessed by internal microbeads control, from slides exposed to shear flow and static control were analyzed by flow cytometry. PPTs were located on the high gate, PLPs in the middle gate, and MkMPs in the low gate. The number of particles in each gate is displayed below each gate. (B) MkMPs were smaller than microbeads of 1.34 μm diameter. (C) Expression of CD41 and CD42b on MkMPs from d12 Mk cells. (D) CD62P expression and the corresponding IgG control of CD41$^+$ MPs from d12 Mk cells. (E) The relative number of CD41$^+$ microparticles generated from d10 or d12 Mk cells either under static conditions (white bars) or upon application of shear flow (grey bars) at 2.5 dyn/cm$^2$ for 0.5 hour (d10 and d12) or 2 hours (d10). (F) At d10 and d12, DMSO (vehicle control, white bars) or z-VAD.fmk (pan-caspase inhibitor, grey bars) or z-DEVD.fmk (caspase-3 inhibitor, black bars) treated Mks were exposed to shear flow at 2.5 dyn/cm$^2$ for 0.5 hour. After shear flow exposure, the number of isolated MkMPs was measured by flow cytometry. The number of MkMPs from one slide of Mks under shear flow was normalized by the number of MkMPs on a slide maintained under static culture conditions, and the resulting ratios were plotted. Error bars indicate SEM of 3 biological replicates. *$P<0.01$ in panel (E) and *$P<0.05$ in panel (F).

When we examined the size distribution of cell fragments released from Mks under both static and shear-flow conditions, in addition to PLPs (d=1-3 μm) and PPTs (d=3-10 μm), we found a distinct population of very small particles (FIG. 8A). We ran a microbead (d=1.34 m) control to confirm that these particles are on an average considerably smaller than 1.34 μm (FIG. 8B). Mature Mks and activated platelets can give rise to MPs that are smaller than platelets. Surface staining demonstrated that most of these particles were CD41$^+$ and CD42b$^+$, but many were also CD41$^+$ and CD42b$^-$ (FIG. 8C). In order to identify the origin of these CD41$^+$ particles, we examined them for CD62P expression. CD62P is expressed on PMPs but not on the MkMPs. We found that ca. 16% of the CD41$^+$ MPs were CD62P$^+$, thus suggesting that most of these MPs were MkMPs deriving from Mks rather than from activated PLPs (FIG. 8D), which presumably can generate MPs similar to PMPs, i.e., CD62P$^+$ MPs.

Cultures of Mk cells post shear exposure contained a dramatically larger number of these MkMPs compared to those from Mks grown under static conditions (FIG. 8A). Thus, Mk exposure to shear results in increased MkMP formation in addition to enhanced PLPs generation. Exposure to 2.5 dyn/cm$^2$ for 0.5 hour resulted in increased MkMPs generation by 24- and 27-fold at d10 and d12, respectively (FIG. 8E). For d10 Mks, exposure to 2.5 dyn/cm$^2$ for 2 hours resulted in a 47 fold increase in MkMPs generation (FIG. 8E). Next, we investigate if caspases mediate the shear stress-enhanced generation of MkMPs. As described earlier, Mks were treated with 10 μM z-VAD.fmk or z-DEVD.fmk before exposed to shear stress at d10 and d12. The ratio of the number of MkMPs from one slide of Mks under shear flow over the number of MkMPs under static conditions was used to assess the effect of shear stress on MkMP generation. The results (FIG. 8F) show that only treatment with caspase-3 inhibitor (z-DEVD.fmk) attenuated the effect of shear stress, suggesting that caspase-3 is involved in shear-enhanced MkMP generation.

Flaumenhaft et al. have shown that the CD41$^+$ MPs in human plasma are mainly derived from Mks rather than activated platelets [5]. However, no mechanism for generating MkMPs was previously known, and no function for MkMPs was known either until this present set of investigations and data. Our data support the thinking that when mature Mks enter BM sinusoids and are exposed to shear circulatory forces, numerous MkMPs are likely formed. While PMP generation from platelets on immobilized von Willebrand-factor (vWF) coated surfaces under high shear was previously shown, it was reported that vWF was necessary for the generation of PMPs under shear flow. These findings pertain to the generation of MkMPs (which are different from the PMPs) under shear flow and without the need for vWF involvement. While the cellular mechanisms leading to membrane vesiculation and MP release remain an active research field, studies from PMP biogenesis suggest that PS externalization and caspase-3 activation play an important role in MP generation. In our study, we found that caspase-3 activation and PS externalization were enhanced by shear stress, thus suggesting that shear-stress enhanced MkMP generation may be mediated by PS externalization and caspase-3 activation. The latter is supported by the data from the caspase-3 inhibition assays.

Example 6. Novel Biological Activity of MkMPs: Promoting Mk Differentiation of HSPCs A physiological function for MkMPs has not been yet previously reported. This is the first study to identify the role and potential use of MkMPs. We hypothesized that a role of MkMPs might be to accelerate hematopoietic-progenitor differentiation into Mks. In early experiments, we found that MkMPs cocultured with HPCs from d5 of Mk culture from CD34$^+$ cells promoted HPC survival and Mk differentiation under serum- and TPO-free conditions. We thus examined in more detail this effect using MPs generated from d12 Mks.

We will refer to these MPs as MkMPs although they may contain a small fraction (ca. 16%) of CD62P$^+$ MPs. MkMPs were cocultured with CD34$^+$ cells in a medium without added TPO but with 50 ng/mL rhSCF (for enhancing cell survival), and the outcomes were examined after 8 days of culture. In more detail, 30,000 CD34$^+$ cells (or cultured HPCs from d3 culture of CD34$^+$ cells with or without TPO) were incubated with 10 MkMPs or PMPs per CD34$^+$ cell or HPC in 50 µL IMDM medium for 1 hour at 37° C. to enhance the contact between MPs and cells. After that, the cells with the MPs were diluted in 300 µL IMDM medium supplemented with 5% BIT9500 and 50 ng/mL rhSCF and cultured at 37° C. and 20% $O_2$. For some coculture, Lin$^+$ cells (CD2$^+$, CD3$^+$, CD11 b$^+$, CD14$^+$, CD15+, CD16$^+$, CD19$^+$, CD56$^+$, CD123$^+$, or CD235a$^+$) from CD34$^+$ cells before coculture with MkMPs. For some coculture of MkMPs and d3 HPCs, cells were harvested after 5 hours of incubation and then processed for TEM imaging. For some cocultures, MkMPs were labeled with fluorescent dye CFDA-SE (Sigma-Aldrich) first and incubated with d3 HPCs for various times before analysis by flow cytometry. For other coculture, cells were harvested on d8 for CD41 and ploidy flow-cytometry analysis. At d9, cells in coculture were examined using multiphoton confocal microscope (Zeiss 510 NLO), and DIC (Differential Interference Contrast) images were collected. At d10, cells from coculture were seeded onto human fibrinogen-coated coverslips and cultured overnight for staining for β1 tubulin (TUBB1), vWF and serotonin (5-HT) at d11. Cells from vehicle control were fixed first and cytospun onto coverslip using Shandon Cytospin 4 (Thermo Scientific) before immunofluorescent staining. At d11, some cells were harvested for TEM imaging.

Figure 9:
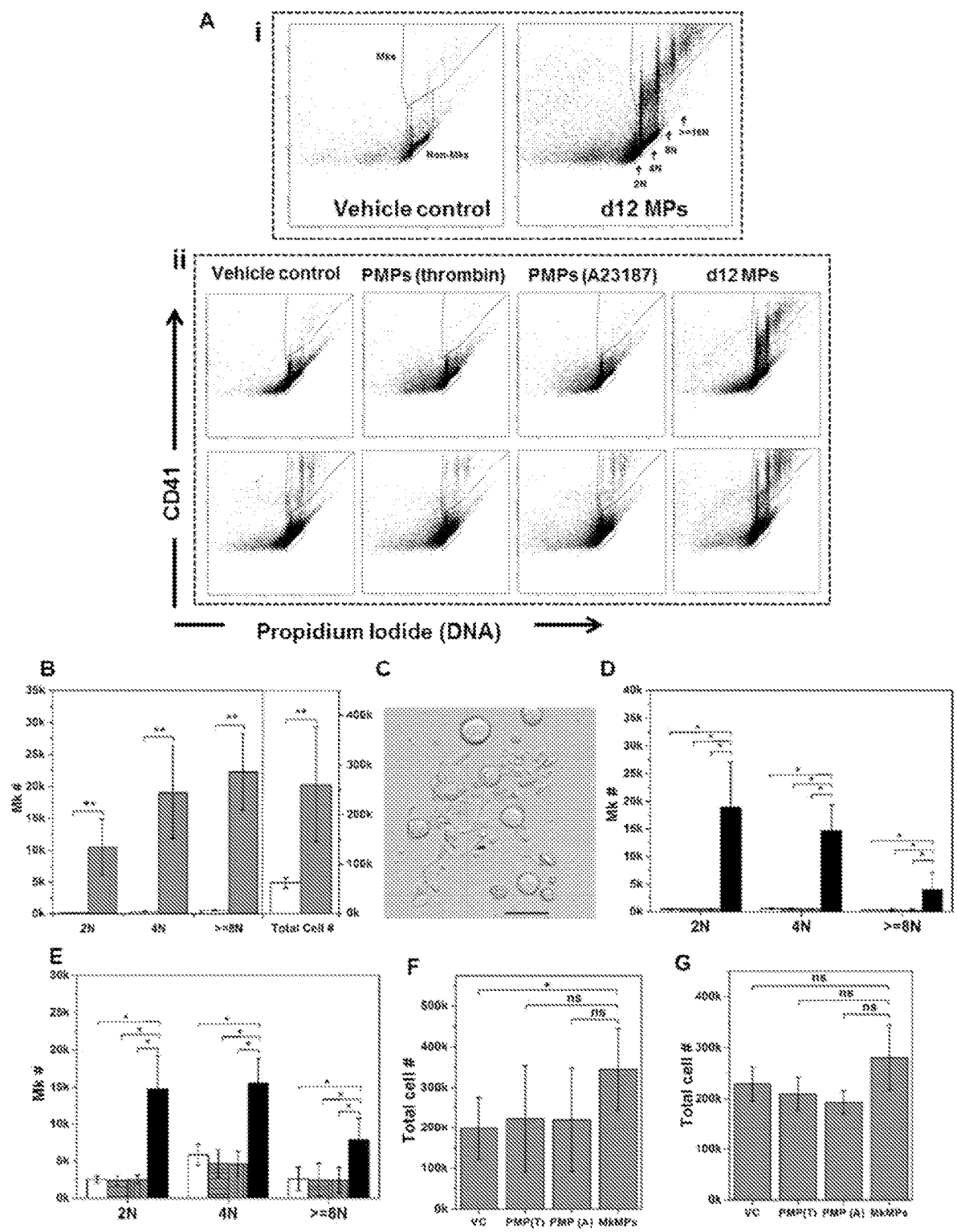
FIG. 9. MkMPs promote Mk differentiation of CD34+ cells and HPCs. (A) Representative graph of flow cytometry ploidy analysis of cells from various coculture conditions at d8. (i) CD34+ cells were cocultured with or without MkMPs starting at d0. (ii) HPCs from d3 culture without (top panel) or with (bottom panel) TPO were cocultured without or with MkMPs, PMPs from d3 to d8. The same fraction of cells from each sample was analyzed. (B, C) At d0, 60,000 CD34+ cells were cocultured with (grey bars) or without (vehicle control, white bars) MkMPs in a medium without TPO. The numbers (B) of total cells and Mks with 2N, 4N and >=8N ploidy were counted at d8. Some Mks started to form PPTs at d9 of coculture (C). (D-G) At d3, 60,000 HPCs from culture with (D, F) or without (E, G) TPO were cultured in TPO-free medium with or without the addition of MkMPs or PMPs. Total cells (F, G) and Mks (D, E) with 2N, 4N and >=8N ploidy were counted at d8. (D, E) The white bars represent vehicle control culture; the grey bars filled with horizontal lines represent coculture with PMPs generated by thrombin stimulation; the grey bars filled with vertical lines represent coculture with PMPs generated by calcium ionophore A23187 stimulation; the black bars represent coculture with MkMPs. (F, G) VC=vehicle control culture; PMP (T)=coculture with PMPs generated by thrombin stimulation; PMP(A)=coculture with PMPs generated by calcium ionophore A23187 stimulation. Error bars indicate SEM of 3~4 biological replicates. *P<0.01; ns, not significant.

In the vehicle control culture, barely any CD34$^+$ cells could differentiate into Mks by d8 (FIG. 9A (i), 9B). However, we observed dramatic induction of Mk differentiation (as assessed by CD41 expression and polyploidization) in the d8 culture of CD34$^+$ cells cocultured since d0 with MkMPs (FIG. 9A (i), 9B). In addition, MkMPs promoted cell proliferation: the total cell number was increased 4.2 fold compared to vehicle control (FIG. 9B). We also examined if MkMPs could stimulate partially differentiated HPCs. CD34$^+$ cells were cultured in medium with or without TPO for 3 days and were then cocultured with MkMPs without TPO for 5 more days to d8. D3 HPCs from culture without TPO gave rise to very few Mks in vehicle control culture, but MkMPs induced dramatically higher (by >10,000 fold) differentiation into Mks (FIG. 9A(ii), 9D) with a concomitant 1.7-fold increased cell expansion (FIG. 9F) compared to vehicle control. In vehicle control cultures, d3 HPCs from culture with TPO developed into Mks by d8 even without further TPO stimulation. However, coculture with MkMPs resulted in 5.9-, 2.7- and 3.0-fold higher numbers of Mks with 2N, 4N and >8N ploidy (FIG. 9A(ii), 9E), although the total cell number was not increased (FIG. 9G). Taken together, these data show that d12 MkMPs promote Mk differentiation of HSPCs at different differentiation stages and that the effect is more pronounced on more primitive, uncultured CD34$^+$ cells.

In order to further characterize the Mks generated from CD34$^+$ cells cocultured with MkMPs, the coculture was prolonged to d11. At d9, we found that some Mks started to form proplatelets (FIG. 9C). At d11, cells were stained for β1 tubulin, vWF and serotonin to examine proplatelet structures, and the formation of α- and dense-granules, respectively. Fluorescent imaging demonstrated that Mks generated from the cocultures displayed normal microtubule proplatelet structures and synthesized both types of platelet granules (FIG. 10A). TEM imaging (FIG. 10B) of Mks from d11 of coculture confirmed that numerous platelet granules were packed in Mk cells, which also displayed the characteristic invaginated membrane system. These data demonstrate that Mks generated from coculture of CD34$^+$ cells with MkMPs display normal developmental characteristics.

Since d12 MkMPs contained ca.16% CD62P$^+$ MPs with PMP characteristics, we examined if PMPs generated from activated human platelets by thrombin or the calcium ionophore A23187 could have an effect similar to that of MkMPs. Compared to vehicle control, coculture of d3 HPCs (from cultures with or without TPO) with either type of PMPs did not affect the Mk differentiation of HPCs compared to control (FIG. 9A(ii), 9D, 9E, 9F, 9G). These data demonstrate that PMPs cannot promote Mk differentiation of HPCs, thus suggesting that the MkMP effect derives from the ~84% of CD62P$^-$ MkMPs.

Although the protocol for generating MkMPs employs rigorous centrifugal enrichment and triple washing in IMDM medium, we wanted to verify that the impact of MkMPs in promoting the Mk differentiation of HSPCs was not due to TPO attached to MkMPs. To this effect, we used a TPO ELISA assay to measure the amount of TPO carried by MkMPs and PMPs. We found that the total TPO carried into the cocultures by the MPs would result in 5.2, 14, 27 pg/mL TPO in HSPC cocultures with PMPs (A23187), PMPs (thrombin) and MkMPs, respectively. This assumes that all TPO becomes available to all HSPCs, which is not true as we found that many MkMPs remain in culture for many days without being attached to cells. No study has tested the effect of TPO at such low concentrations. The lowest TPO level examined is 100 pg/ml, which has only a small impact on Mk differentiation compared to saturation TPO levels. In support of the argument that the impact of MkMPs does not derive from the small amount of TPO carried into the coculture, we note that the TPO carried by the thrombin-generated PMPs (which had no Mk-differentiation impact on HPCs) was about half that carried by MkMPs.

Figure 10:
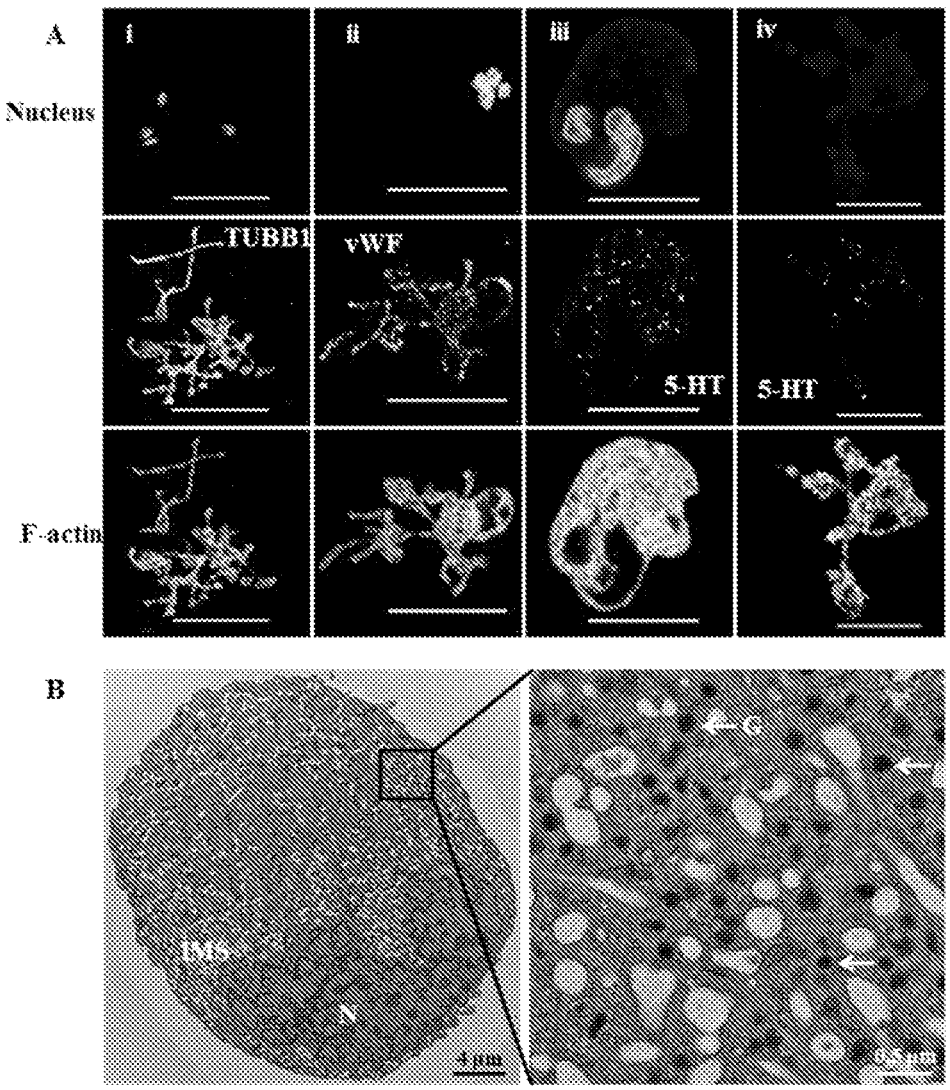
FIG. 10. Mks generated from MkMP coculture display characteristic PPT structures and synthesize both alpha- and dense-granules. CD34+ cells were cocultured with MkMPs starting at d0. (A) At d11, cells were stained for beta 1 tubulin (i, TUBB1), vWF (ii) and serotonin (iii and iv, 5-HT) to visualize PPT structures, alpha-granules and dense-granules, respectively. Panels (iii) and (iv) displaying serotonin staining of both cells with a nucleus (panels iii) and anuclear cellular fragments (PPTs; panels iv) to demonstrate the development of early development of dense-granules in cells prior to fragmentation. Scale bar: 50 μm in panel (i, ii) and 20 μm in panel (iii, iv). (B) TEM thin section of a Mk from d11 of the coculture. IMS: Invaginated Membrane System; N: Nucleus; G: Granules.

This is the first study ever to show that true MkMPs have a biological role in inducing megakaryocytic differentiation of HSPCs in the absence of TPO and to do so in a physiological significant way leading to the formation of biologically active proplatelets as shown in FIG. 10. These data support our claims for producing and using MkMPs for cells for applications in Transfusion Medicine to promote in vivo and in vitro (ex vivo) de novo megakaryopoiesis and platelet biogenesis without using TPO in in vivo applications.

Example 7: MkMPs are Produced Largely by Mature Mk Cells

Figure 11:
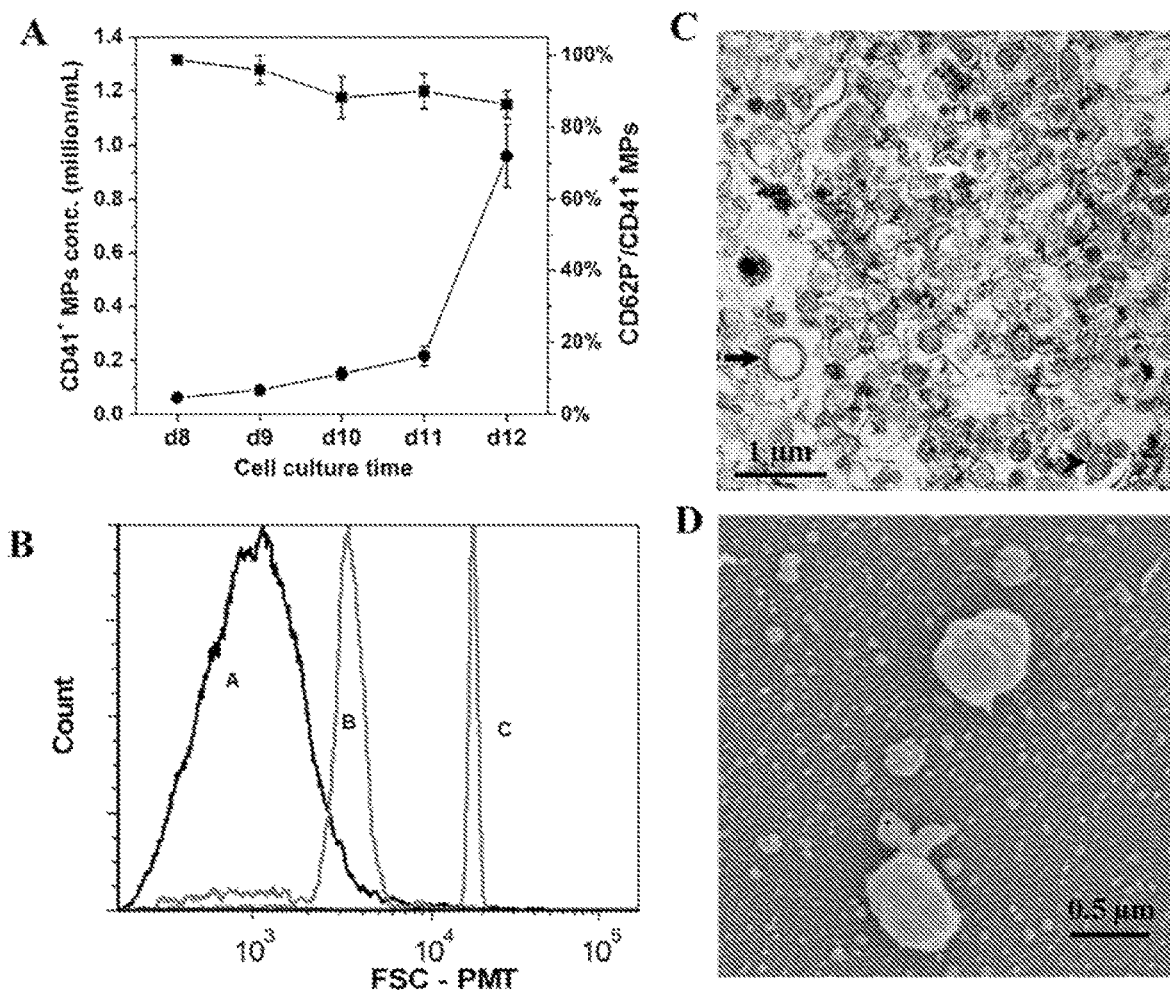
FIG. 11. Characterization of megakaryocyte-derived MPs (MkMPs). (A) CD62P expression and concentration of CD41+ MPs in Mk culture from d8 to d12. At d7, enriched Mk cells were cultured at fixed concentration of 200 k/mL. From d8 to d12, 100 μL cell culture medium was harvested every day for CD41 and CD62P analyses by flow cytometry. MP concentration was counted by flow cytometry using internal microbeads as control. The line with squares represent CD62P− level and the line with circles represents CD41+ MP concentration. Error bar represents standard error of mean (SEM) of 3 biological replicates. (B) Representative size distribution histogram of MkMPs (line A) from d12 cell culture analyzed by flow cytometry using microbeads with diameter 0.88 μm (line B) and 1.34 μm (line C) as internal size standards. Representative TEM (C) and SEM (D) micrographs of MkMPs from d12 cell culture.

We have shown above in Example 6 that Mks can shed CD41+CD62P$^-$ MPs (i.e., MkMPs), and that exposure to fluid shear stress could enhance this process by more than 20 fold in terms of numbers of MkMPs produced. In order to investigate MkMP generation in details under static conditions, CD34$^+$ HSCs were induced to differentiate into Mks as previously described. At d7 of cell culture, Mks were enriched (CD41$^+$: >95%) and seeded in fresh medium at concentration of 200,000 cells/mL. Concentration and CD62P expression of CD41$^+$ MPs in Mk cell culture were measured by flow cytometry from d8 to d12. The data show that more than 85% of CD41$^+$ MPs in cell culture from d8 to d12 were CD62P$^-$, indicating that most of CD41$^+$ MPs were derived from Mks rather than platelet-like particles (PLPs) (FIG. 11A). The data also show that Mks at immature stage released MkMPs slowly from d8 to d11 and the concentration of MkMPs in cell culture was increased by ~50% every day (FIG. 11A). However, Mks shed more MPs and MkMP concentration was increased dramatically by 4.4 fold from d11 to d12 (FIG. 11A) when mature Mks displayed extensive proplatelets but few PLPs were generated.

Example 8: Characterization of MkMPs Produced from Mature Mk Cells

We used MkMPs from d12 cell culture in the following studies. Through successive centrifugation, MkMPs were isolated from cell culture and processed for flow cytometric and electron microscopic analyses to obtain the size distribution of MkMPs. The flow cytometry data demonstrate that most of MkMPs were smaller than microbeads with diameter of 0.88 μm (FIG. 11B). This result was confirmed by TEM and SEM analyses (FIGS. 11C and 11D). In addition, TEM micrograph also shows that very few particles were smaller than 100 nm, indicating that we did not enrich exosomes (40-100 nm) with MkMPs from cell culture using our centrifugation protocol. We observed that TEM staining of some MkMPs (indicated by black arrow) was very light while the staining of others (indicated by arrow head) was very dense (FIG. 11C). In addition, some MkMPs (indicated by white arrow) even carried several smaller particles inside them (FIG. 11C). These observations indicate that MkMPs were not uniform with respect to their size and internal content. As shown by SEM micrographs, MkMPs were not spherical and their membrane was not smooth (FIG. 11D).

Figure 12:
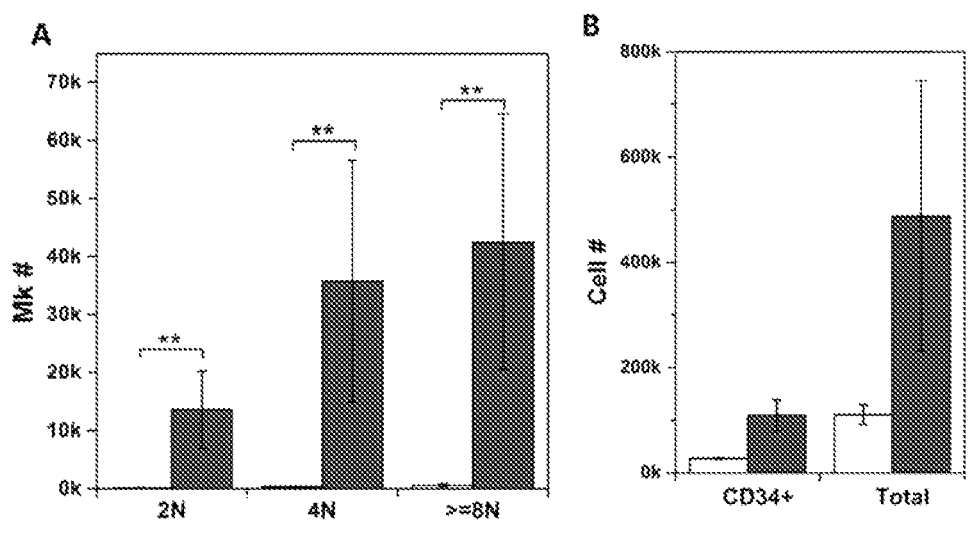
FIG. 12. MkMPs promote Mk differentiation of the primitive CD34+Lin− stem cells. The primitive Lineage− cells were enriched from CD34+ cells and cocultured with MkMPs at concentration of 10 MkMPs/cell for 8 days. (A) The numbers of Mks with different ploidy levels (2N, 4N and >=8N) in the control culture and the MkMP coculture at d8. (B) The numbers of CD34+ cells and total cells in the control culture and the MkMP coculture at d8. The white bars represent vehicle control culture and the grey bars represent MkMP coculture. Error bar represents SEM of 3 biological replicates. **, P<0.01.

Example 9: MkMPs Target with Even Higher Effectiveness the Most Primitive Hematopoietic Stem Cells, Namely the CD34+ Lin− Cells. Significantly, MkMPs Also Promote the Expansion of the CD34+ HSPCs In example 6, we showed that MkMPs could induce and enhance differentiation of CD34+ HSPCs and partially differentiated HPCs from d3 and d5 Mk culture to Mks that were functional to project PPT and synthesize both α- and dense-granules without additional exogenous TPO stimulation. Here, we wanted to show that MkMP cells target also the least differentiated of the HSPC CD34+ cells, the Lineage negative (Lin−) cell by removing the committed Lineage positive (Lin+) cells namely the CD2+, CD3+, CD11b+, CD14+, CD15+, CD16+, CD19+, CD56+, CD123+, or CD235a+ cells. This was achieved using the lineage cell depletion kit from Miltenyi Biotec. A total of 60,000 CD34+ Lin− cells were incubated with 10 MkMPs/cell in 50 μL IMDM medium for 1 hour at 37° C. to enhance the contact between MkMPs and target cells. After that, coculture of MkMPs with CD34+ Lin− cells were diluted in 600 μL IMDM medium supplemented with 5% BIT9500 and 50 ng/mL rhSCF, and cultured at 37° C. and 20% O2. All cocultures were maintained for 8 days before harvest for ploidy assay and analysis by flow cytometry. CD34+ Lin− cells at d0 and cells from coculture at d3, d5 and d8 were stained with CD41, CD34, CD11 b and CD235a antibodies and analyzed by flow cytometry. Flow cytometry analysis shows that MkMP coculture had a large amount of Mks with 2N, 4N and >=8N ploidy classes while very few Mks were found in the vehicle control culture (FIGS. 12A and 12B). In addition, there were more total cells in MkMP coculture than in control culture (FIG. 12B). These results demonstrate that MkMPs were able to induce differentiation of Lin−CD34+ cells into the Mk lineage.

In order to find out what are the CD41− cells are in the MkMP coculture, cells from the cocultures and control cultures were stained with anti-CD34, CD41, CD11 b and CD235a antibodies to identify HSPCs, Mks, granulocytes and erythrocytes, respectively, and analyzed by flow cytometry. The results show that very few cells differentiated into granulocytes or erythrocytes in either the vehicle control culture or the MkMP coculture, indicating that MkMPs could not induce HSCs differentiation to these two lineages. This shows that the effect of MkMPs on HSPCs is specific to the Mk lineage differentiation and supports the claims related to outcome specificity for in vivo applications, i.e., that MkMPs promote ONLY the Mk differentiation of HSPCs.

In the MkMP coculture, the percentage of CD41+ cells increased from 0% at d0 to ~47% at d5 and plateaued after d5, indicating that 5 days are sufficient for HSCs to commit to Mk lineage induced by MkMPs. From the ploidy analysis, the percentage of CD41+ cells in coculture at d8 was about 19% which is lower than the ~48% obtained from the surface marker staining analysis. This could be due to the assay methodology since we always obtained lower CD41 percentages from ploidy analysis than surface marker staining. This could be also contributed partially by the possibility that CD41− cells with CD41+ MkMPs attached were detected by flow cytometry as CD41+ cells in surface-marker staining analysis but not in ploidy assay. Compared to the vehicle control culture, the coculture also had a higher percentage of CD34+ cells at d8 (47% vs. 28%) and based on the total cell number obtained from ploidy assay, there were more CD34+ cells in coculture than control culture (108 k vs. 27 k, FIG. 12B). These results show that MkMPs have two biological effects on HSPCs: promote expansion of CD34+ cells and induce Mk differentiation of CD34+ HSPCs. These findings are novel, and support the use of MkMPs for cell for applications in Transfusion Medicine and stem-cell transplantation.

Example 10. Target Specificity: MkMPs could not Trans-Differentiate Human Granulocytes, MSCs and HUVECs into Mk Cells Previous studies have demonstrated that certain types of cells can trans-differentiate into other unrelated types of cells It is possible that cell-derived microparticles mediate trans-differentiation. For example, microparticles derived from lung endothelial cells induced trans-differentiation of bone marrow cells into endothelial cells. To investigate if MkMPs could trans-differentiate other cell types into Mks, we tested human granulocytes, MSCs and HUVECs, all of which are encountered by MkMPs in the bone marrow environment or in circulation.

Figure 13:
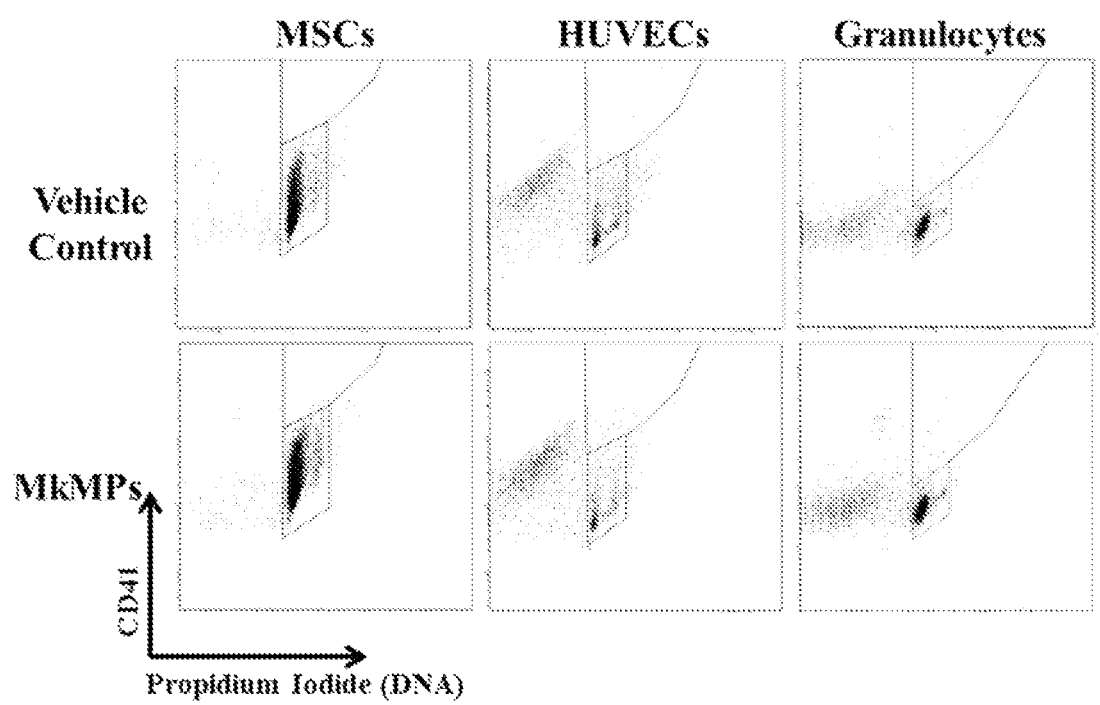
FIG. 13. Representative CD41 expression and ploidy analyses of MkMP coculture with MSCs, HUVECs or granulocytes. Human MSCs (passage 2-4), HUVECs (passage 3-5) and CD34+ cell-derived granulocytes were cocultured with MkMPs at the concentration of 10 MPs/cell for 8 days before harvested for CD41 expression and ploidy analyses by flow cytometry. The results represent two biological replicates. The top gates represent CD41+ cells (Mks) and the bottom gates represent CD41 cells.

A total of 60,000 HUVECs (human umbilical cord vascular endothelial cells; passage 3-5, obtained from ATCC), MSCs (mesenchymal stem cells; passage 2-4, donation from Prof. Xinqiao Jia, Univ of Delaware) or enriched CD15+ granulocytes were incubated with 10 MkMPs/cell in 50 μL IMDM medium for 1 hour at 37° C. to enhance the contact between MPs and cells. After that, coculture of MkMPs with MSCs and granulocytes were diluted in 600 μL IMDM medium supplemented with 5% BIT9500 and 50 ng/mL rhSCF, and cultured at 37° C. and 20% O2 and coculture of MkMPs with HUVECs were diluted in 600 μL growth medium without any endothelial cell growth factors. All cocultures were maintained for 8 days before harvest for ploidy assay and analysis by flow cytometry. Flow cytometry analysis (FIG. 13) shows that no CD41+ or polyploid cells were observed after 8 days of coculture of MkMPs with granulocytes, MSCs or HUVECs, indicating that MkMPs could not trans-differentiate these types of cells into the Mk lineage and thus the action of MkMPs is target-specific. MkMPs may only affect the fate of HSPCs but not MSCs or other mature cells like granulocytes or HUVECs. This target specificity may be caused by the inability of these three types of cells to internalize MkMPs because they are lacking suitable surface receptors to mediate MP uptake or the inability of signaling molecules carried by MkMPs to induce trans-differentiation. These novel findings support our claim for the exquisite specificity of MkMP to ONLY target HSPCs and no other related cells like HUVECs, MSCs, or granulocytes. This shows that MkMPs can be used for in vivo animal or human transplantation to specifically and uniquely target HSPCs in vivo, and thus support our claims to that effect.

Figure 14:
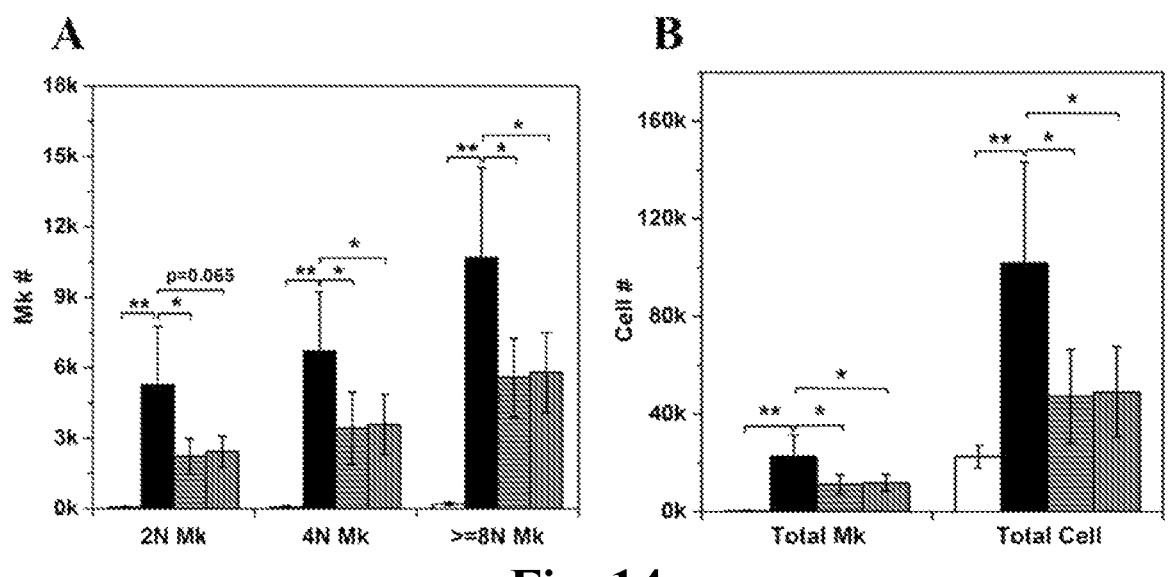
FIG. 14. RNase treatment reduces the inducing effect of MkMPs on HSCs. CD34+ cells were cocultured with MkMPs (10 MkMPs/cell) treated with or without RNase (RNase A/T1 cocktail or RNase ONE) for 8 days before harvested for ploidy analysis by flow cytometry. (A) The cell numbers of Mks with different ploidy levels (2N, 4N, >=8N) in various cell cultures at d8. (B) The numbers of total Mks and total cells in various cell cultures at d8. The white bars represent vehicle control culture. The black bars represent coculture with MkMPs without treatment. The grey bars filled with horizontal lines represent coculture with MkMPs with RNase A/T1 treatment. The grey bars filled with horizontal lines represent coculture with MkMPs with RNase ONE treatment. Error bar represents SEM of 4 biological replicates. *, P<0.05; **, P<0.01.

Example 11. MkMPs Promote Mk Differentiation Through Transfer of the RNA Carried by the MkMPs Several studies have reported that signaling molecules carried by MPs, including ESC-derived MPs, MSC-derived MP and PMPs, are RNA (mRNA and/or miRNA) and MPs exert their biological function through RNA transfer to target cells. To investigate if MkMPs induce Mk differentiation of HSPCs through RNAs, MkMPs were treated with RNase to degrade if possible the RNA carried by these MkMPs and cocultured with HSPCs, similar to what previous studies have reported. Two different commercial RNases, the RNase A/T1 cocktail from Ambion and the RNase ONE™ from Promega, were used in this study and ploidy analysis was used to examine the effect of RNase treatment. As expected, we found that MkMPs without RNase treatment induced Mk differentiation of HSCs and increased the total cell number while no differentiation was observed in vehicle control culture (FIG. 14). The numbers of 2N, 4N and >=8N Mks as well as total Mks and other cells was decreased by ~50% by either type of RNase treatment (FIG. 14). RNase treatment did not totally abolish the effect of MkMPs on HSCs. This could be due to incomplete digestion of RNA, especially miRNA which is more RNase-resistant than mRNA and has been proposed to be mainly responsible for the biological effects of other MPs. Another possible reason is that proteins carried by MkMPs may be also involved in inducing Mk differentiation, like ESC MPs and tumor MPs whose biological functions are dependent on both of protein and RNA transfer. Here, we demonstrated that MkMPs induce differentiation of HSPCs towards to Mks, partially at least, through the carried RNAs.

Example 12. MkMPs Interact with Target Cells Through Endocytosis and Membrane Fusion Next, we examined detailed mechanisms through which MkMPs exerted their impact on HSPCs. Although it has been proposed that MP may interact with or be taken up by target cells through direct fusion and endocytosis, there is no information disclosed as to how MkMPs interact and may transfer molecules they contain to target cells. To investigate the mechanisms by which MkMPs interact with target cells and notably HSPCs, MkMPs were stained with cell cytoplasmic tracker dye CFDA-SE and then cocultured with hematopoietic progenitor cells (HPCs) from d3 of Mk culture. After cultured for certain time as indicated below, cells were processed for flow cytometric and microscopic analyses.

Figure 15:
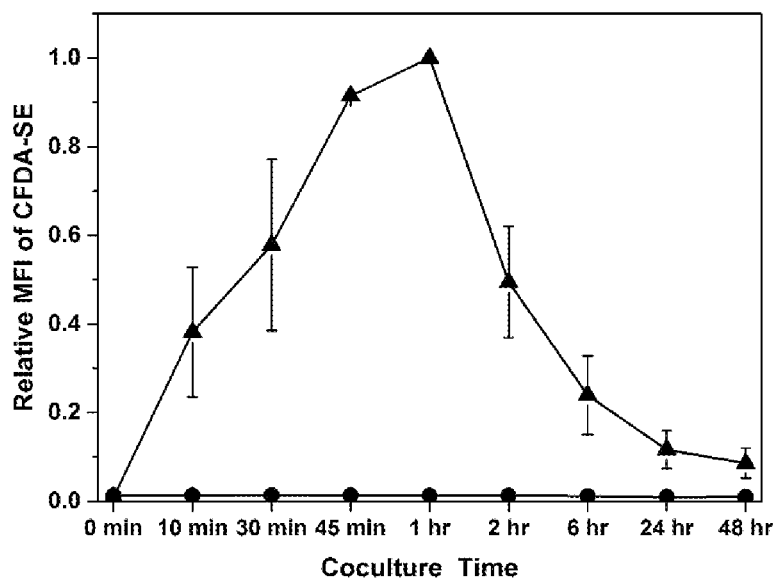
FIG. 15. Kinetics of MkMP binding to cells. MkMPs were stained with dye CFDA-SE and then cocultured with d3 hematopoietic progenitor cells (HPCs). At the time as indicated, some cells were harvested for analysis of mean fluorescence intensity (MFI) of CFDA-SE by flow cytometry. All CFDA-SE MFI at different time points were normalized to MFI at 1 hour time point. The line with circles represents vehicle control sample and the line with triangles represents MkMP coculture. Error bar represents as SEM of 3 biological replicates.

The coculture was firstly analyzed by flow cytometry to examine the kinetics of MkMP binding to cells. At each indicated time point, some cells were harvested from coculture with CFDA-SE stained MkMPs for measurement of mean fluorescence intensity (MFI) of CFDA-SE. The results show that CFDA-SE MFI of cells increased dramatically within one hour of coculture and reached the maximum level at one hour (FIG. 15). As coculture continued, CFDA-SE MFI of cells decreased and plateaued around 24 hours (FIG. 15). These data indicate that MkMPs bind to cell surface very quickly within one hour. After one hour of coculture time, CFDA-SE MFI of cells decreased and this could be caused by the dilution during cell proliferation and the possibility that some MkMPs may dissociate from the cell surface.

Figure 16:
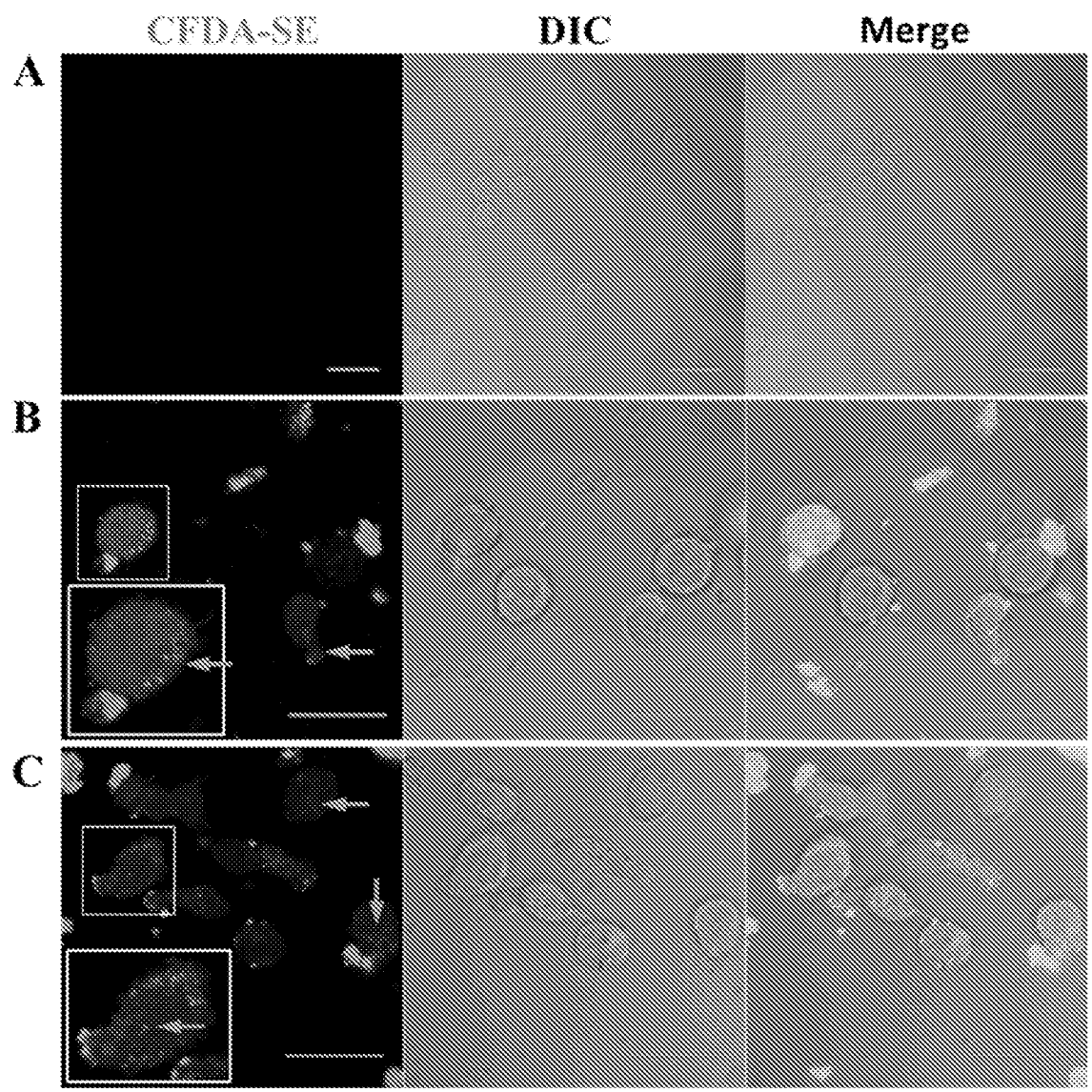
FIG. 16. Uptake of MkMPs by HPCs is through endocytosis while PMPs are not taken up by HPCs. MkMPs and PMPs were stained with CFDA-SE (Green) dye and then cocultured with HPCs for 3-5 hours. Fluorescent and Differential Interference Contrast (DIC) images were collected using confocal microscopy. (A) Vehicle control culture. (B, C) Two images of the MkMP coculture (~4 hours). Scale bar, 20 μm.

Since flow cytometry cannot differentiate MP binding to cells and uptake of MkMPs by cells, coculture of MkMPs and HPCs was examined under confocal microscopy to directly visualize the interaction between live cells and MkMPs. After 3-5 hours of coculture, we observed that most HPCs contained CFDA-SE dye of variable intensity (FIGS. 16B and 16C) and this indicates uptake of MkMPs and thus transfer of dye from MkMPs to cells. Further analyses demonstrated that uptake of MkMPs was through two different mechanisms: endocytosis and direct fusion. We found that some cells contained various numbers of distinct CFDA-SE fluorescence dots representing intact MkMPs that were not clearly associated with the target-cell membrane (FIGS. 16B and 16C, arrow head and FIG. 17), suggesting that these MkMPs were inside the cells. To confirm this finding, images of cells from different confocal planes with 0.4 μm interval were collected to make up a z-stack and 3D images were reconstructed from z-stacks. As demonstrated in 3D images of cells from coculture, intact MkMPs (concentrated green dots) "move" at a shorter distance than the cell edge, delineated by a dim green signal, when the cell rotates along a central axis, indicating that these MkMPs were inside the cell rather than on the cell membrane. These data demonstrate that intact MkMPs were internalized by cells through cell endocytosis.

Figure 17:
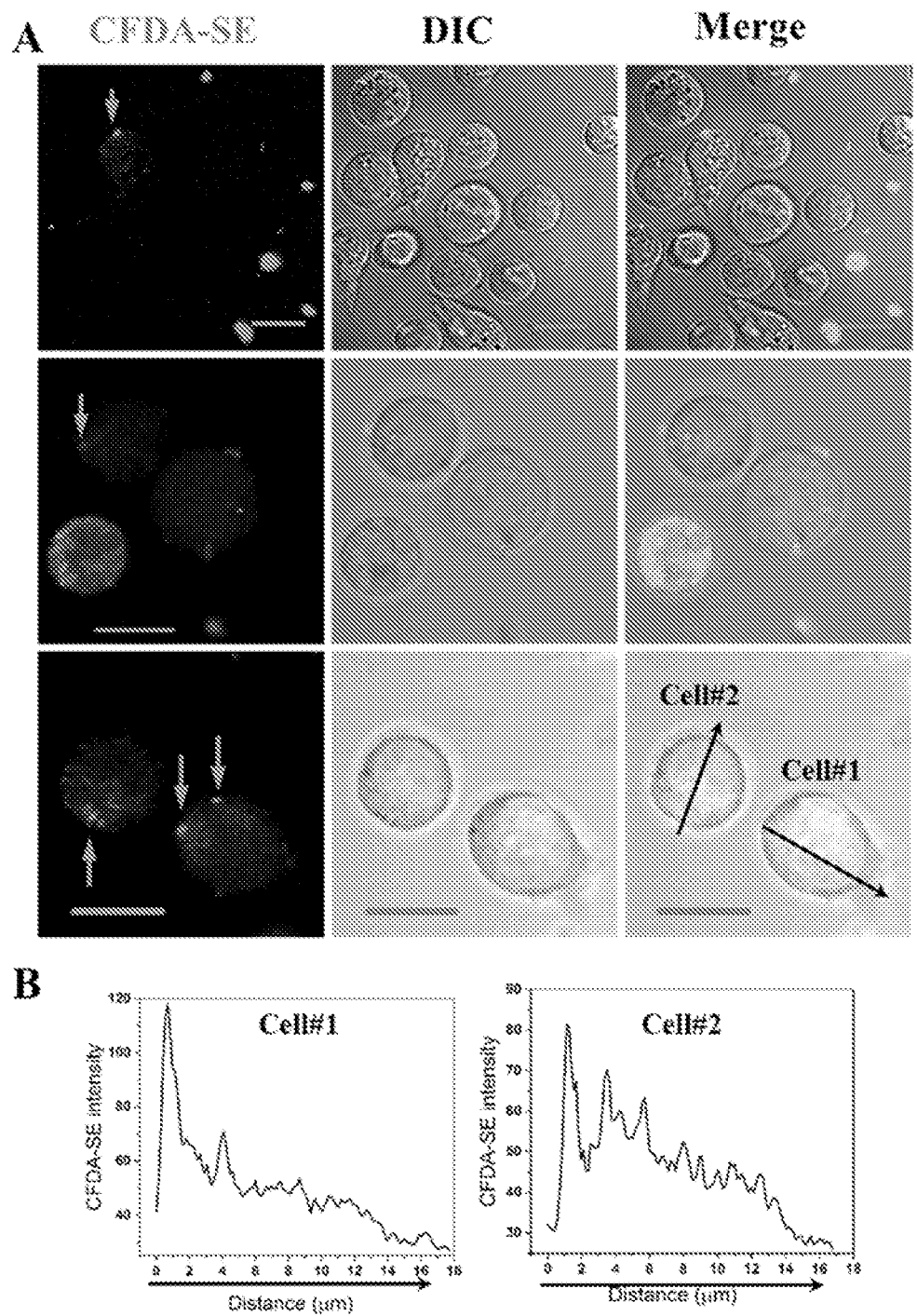
FIG. 17. Uptake of MkMPs by HPCs is through direct fusion as shown by confocal microscopy. MkMPs were stained with CFDA-SE (Green) dye and then cocultured with HPCs for 3-5 hours. Fluorescent and Differential Interference Contrast (DIC) images were collected using confocal microscopy. (A) Three images of the MkMP coculture demonstrate CFDA-SE dye gradient inside the cells (red arrow). (B) CFDA-SE dye intensity profiles of the cell #1 and #2 in panel (A) along black arrows. Scale bar, 20 μm.

In addition to cell internalizing intact MkMPs, we also observed that a gradient of CFDA-SE dye distributed inside some cells and this gradient started from one MkMP on the cell membrane as indicated by the highly concentrated dye (FIG. 17). This CFDA-SE dye gradient may have resulted from MkMPs fusing with the cell membrane, and following that, CFDA-SE dye being discharged directly from the MkMP into the cell cytoplasm. To further confirm that direct fusion mediates this dye gradient formation, cells from MkMP coculture was examined using scanning electron microscopy (SEM) to capture the interaction between MkMPs and cells in details.

Figure 18:
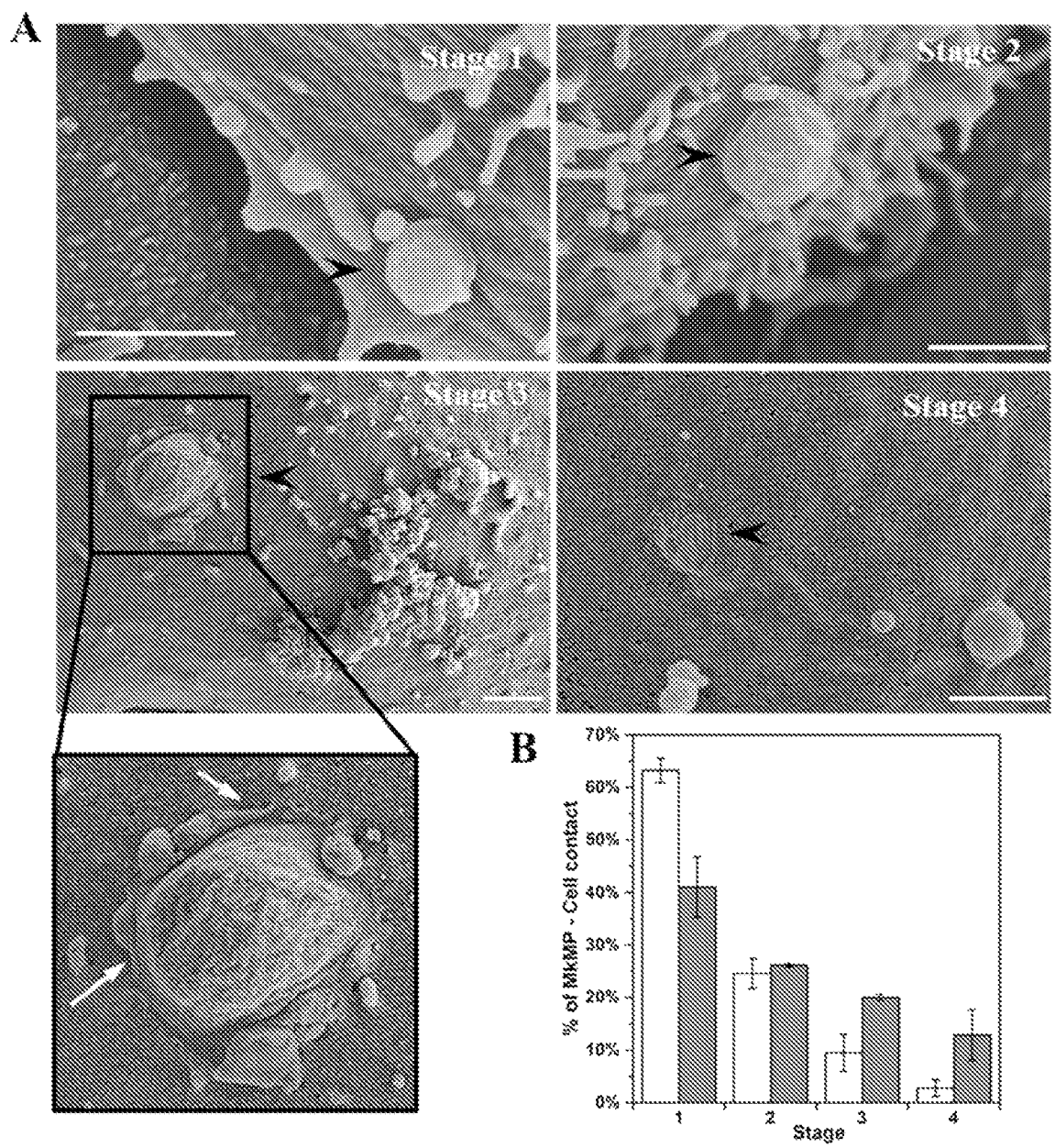
FIG. 18. Uptake of MkMPs by HPCs is through direct fusion as shown by scanning electron microscopy. HPCs were cocultured with MkMPs for 3 and 5 hours and examined using scanning electron microscopy. (A) Representative electron micrographs demonstrate the 4 gradual stages through which MkMPs (black arrow head) were fused into cells. Scale bar, 1 μm. (B) The percentages of the MkMP-cell interaction at each stage after 3 (white bars) and 5 (grey bars) hours of coculture. Error bars indicate SEM of 2 biological replicates.

SEM micrographs of cells from coculture (3-5 hours) show that MkMPs interacted with through a membrane fusion process (FIG. 18A). Some MkMPs were bound to the cell surface and some were partially fused into the cell (FIG. 18A), confirming that direct fusion took place in MkMP coculture. SEM micrographs reveal 4 gradual stages (FIG. 18A) through which MkMPs fused into cells based on the relative volume of MkMPs left outside of the cell membrane. At the $1^{st}$ stage, MkMPs attached to the cell surface by remaining as an intact sphere; at the $2^{nd}$ stage, MkMPs were partially incorporated and less than half of their body was merged with cells; at the 3$^{rd}$ stage, MkMPs were half fused into HPCs with formation of lamellipodia-like structures extending from the MkMP at the contact area with the cells (FIG. 18A, white arrow); at the 4$^{th}$ stage, whole MkMPs were fused into cells and an almost flat MkMP membrane with wrinkles was left on the cell membrane. To the best of our knowledge, these four stages of MP-cell fusion and lamellipodia-like structures have not been reported in the literature before. We also quantified the percentage of MkMP-cell interaction at each stage after 3 and 5 hours of coculture (n=2 biological replicates). Most (~63%) of fusion events were at the 1$^{st}$ stage and very few (~9.7 and ~2.8% respectively) were at the 3$^{rd}$ and the 4$^{th}$ stages when MkMPs were cocultured with HPCs for 3 hours (FIG. 18B). The fusion event at the 1$^{st}$ stage decreased to ~41% while the percentage of fusion events at the 3$^{rd}$ and 4$^{th}$ stages increased to ~20% and ~12.9%, respectively, after the coculture time increased to 5 hours (FIG. 18B), indicating that MP-cell fusion took place continuously in the MkMP coculture.

Figure 19:
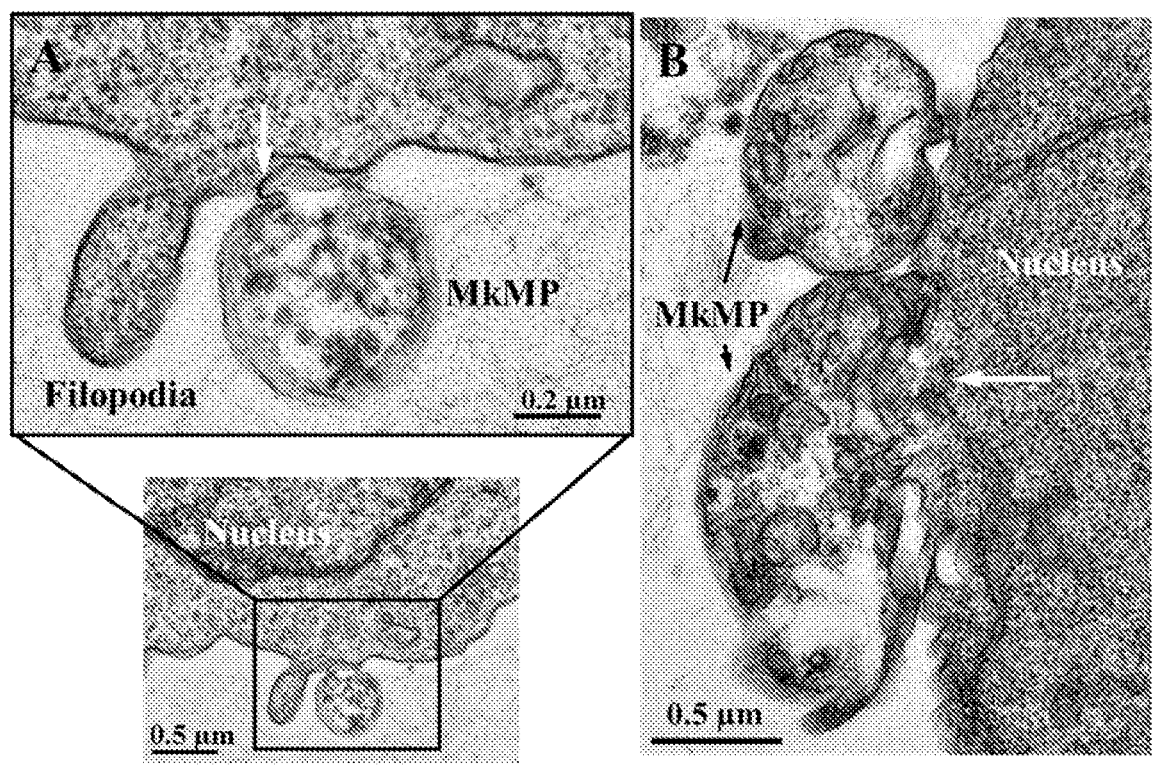
FIG. 19. Uptake of MkMPs by HPCs is through direct fusion as shown by transmission electron microscopy. HPCs were cocultured with MkMPs for 3~5 hours and examined using transmission electron microscopy. (A) One MkMP interacted with one cell and displayed lamellipodia-like structure (white arrow). (B) Two MkMPs interacted with one cell. The membrane between the cell and the MkMP at the bottom was diminished.

In order to capture the internal structures of the MkMP-cell fusion, cells from coculture were processed for TEM analysis. We captured MkMPs bound to cell surface in TEM micrographs (Data not shown). However, we did not successfully capture MkMP-cell fusion events at all four stages identified in SEM micrographs. A possible reason could be that since TEM examines one ultrathin slice of cell samples, the chance that the ultrathin slice contains one MkMP is low. Nevertheless, two MkMPs fused with cells were found in TEM micrographs (FIG. 19). These particles were considered as MkMPs rather than MPs from the cell themselves or part of the cell body based on that they had totally different internal texture and composition from the cell body. The MkMP in the FIG. 19A shows lamellipodia-like structures (white arrow), which we found previously in SEM micrographs on the cell membrane around the contact area with the MkMP. We found that two MkMPs interacted with one cell in the second TEM micrograph (FIG. 19B). The top MkMP is only binding to cell surface without any fusion sign (FIG. 19B). In contract, the membrane (white arrow) between the MkMP at the bottom and the cell body was diminished, demonstrating that the MkMP was partially fused into the cell (FIG. 19B).

This is the first disclosure ever as to of the mechanism by which MkMPs interact with and target HSPCs and supports our claims for the use of unmodified and modified MkMPs.

Figure 20:
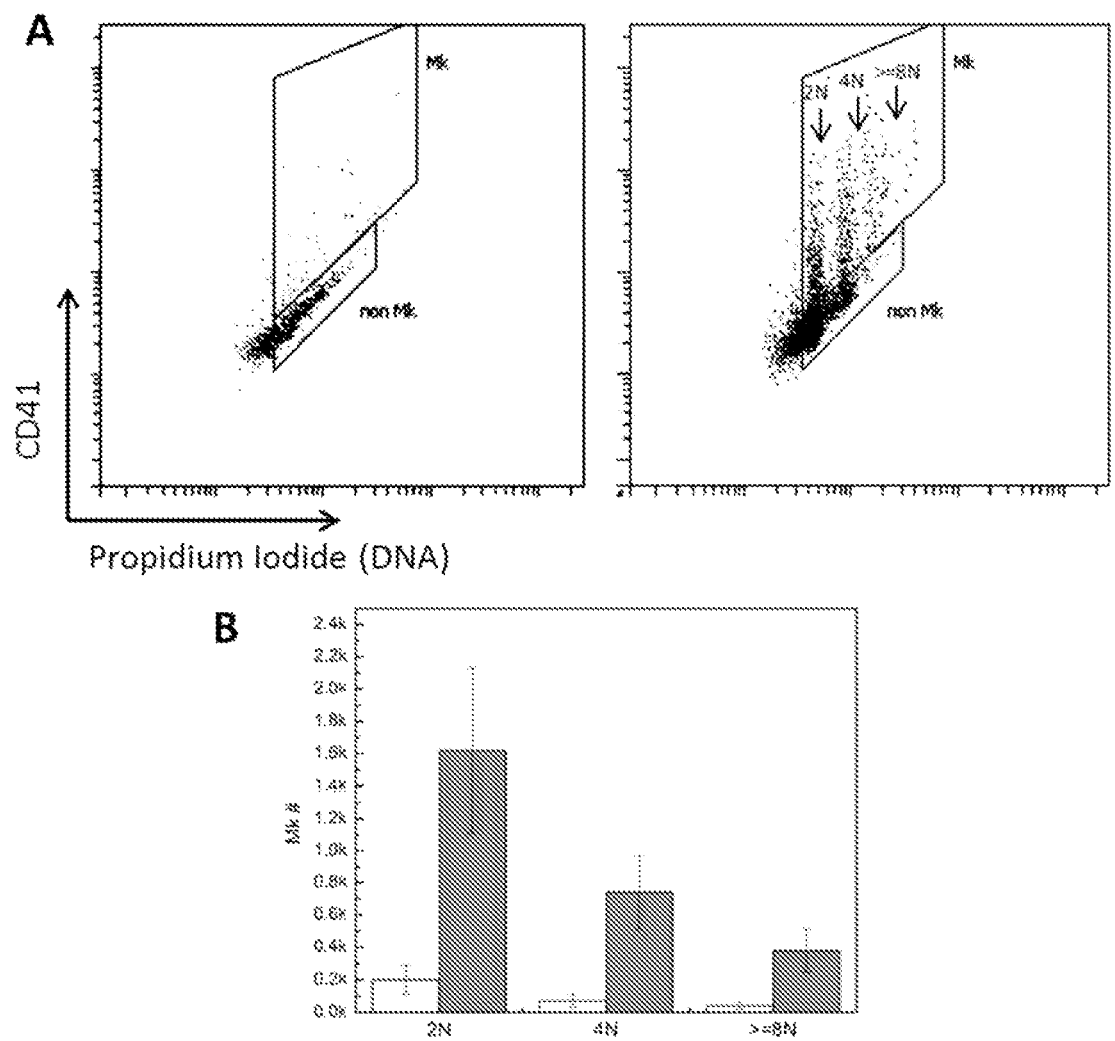
FIG. 20. CHRF-derived MPs (CMPs) induce Mk differentiation of hematopoietic stem cells (HSCs). HSCs were cocultured with or without (vehicle control) CMPs at the concentration of 50 MPs/cell for 8 days without thrombopoietin in culture medium. Cells were harvested for CD41 and DNA staining and analyzed by flow cytometry. (A) Representative flow analysis of ploidy and CD41 expression of cells from vehicle control culture and CMPs coculture. (B) Cell numbers of Mks with different levels of ploidy. The white bars represent vehicle control culture and the grey bars represent coculture with CMPs. Error bars indicate standard error of mean (SEM) of 3 biological replicates.

Example 13. Generation of MkMPs (Termed CMPs) from the Human Megakaryocytic Cell Line CHRF and Demonstration that CMPs can Also Induce and Promote Mk Differentiation of HSPCs CMPs were generated from d3 phorbol 12-myristate 13-acetate (PMA)-induced CHRF cells. 40000 HSCs were coculture with or without CMPs at the concentration of 50 MPs/cell for 1 hr at 37° C. in 50 mL IMDM in the medium to increase CMP-cell contact. Cells with or without CMPs were then diluted into 600 mL medium without thrombopoietin (IMDM, 5% BIT9500, 50 ng/mL rhSCF) at 37° C. and 20% O$_2$ for 8 days. Cell were harvested on d8 for CD41 and DNA staining and analyzed of CD41 expression and ploidy by flow-cytometry (FACSAria II, BD bioscience). Collected CMPs were cocultured with HSCs at the concentration of 50 MPs/cell for 8 days. From the analysis of ploidy flow-cytometry, FIG. 20A shows that HSCs in coculture became Mks with the properties of CD41 expression and polyploidy. The number of Mk of coculture is larger than Mk of control (FIG. 20B). These data show that CMPs are able to induce Mk differentiation of HSCs. Although CMPs may not be suitable for routine applications in human therapy, they can be used to test various processes necessary for the application of primary MkMPs, as a surrogate.

Figure 21:
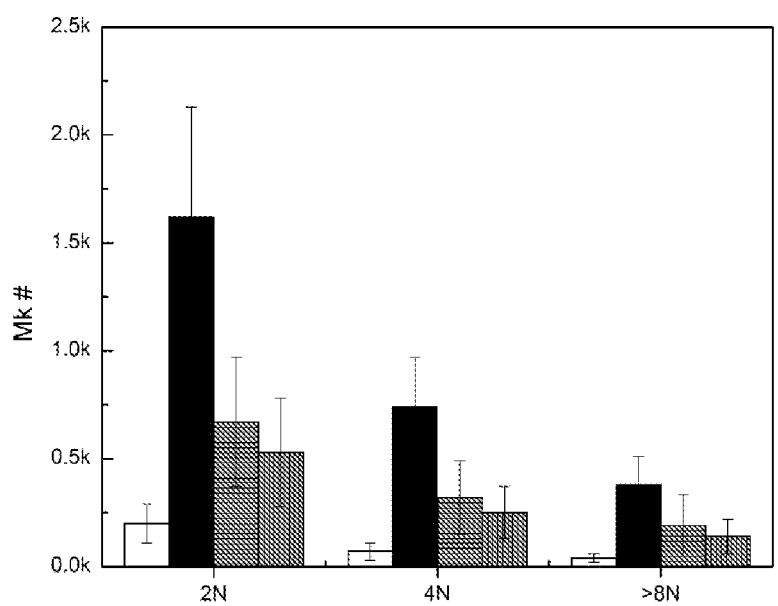
FIG. 21. The effect of RNase treatment on CHRF-derived MPs (CMPs) inducing Mk differentiation of hematopoietic stem cells (HSCs). CMPs were first treated with or without RNase A/T1 or RNase ONE for 1 hr at 37° C. RNase inhibitor, SUPERase-In, were added to stop RNase reaction. HSCs were then cocultured with CMPs or with RNase-treated CMPs or without CMPs at the concentration of 50 MPs/cell for 8 days. The white bars represent vehicle control culture; the black bars represent coculture with untreated CMPs; the grey bars filled with horizontal lines represent coculture with CMPs treated with RNase A/T1; the grey bars filled with vertical lines represent coculture with CMPs treated with RNase ONE. Cells were analyzed of ploidy and CD41 expression by flow cytometry. Cell numbers of Mks with different levels of ploidy were shown in figure. Error bars indicate standard error of mean (SEM) of 3 biological replicates.

Example 14. RNase Treatment is Effective in Eliminating ("Unloading") the Native RNA in Megakaryocytic Microparticles so that they can be Loaded with Desirable Molecules for Delivery to Target HSPCs We used CMPs as a model for primate MkMPs. In example 11, we have shown that RNase treatment can partially abrogate the impact of MkMPs on HSPCS. Here we optimized the process of RNase treatment to remove the RNA content of CMPs. HSPCs were coculture with CMPs, or RNase-treated CMPs, or without CMPs (Control) for 8 days. In detail, CMPs were collected as mentioned previously, and were treated with 1 U/mL RNase A/T1 (Ambion) or 10 U/mL RNase ONE (Promega) under the condition of 37° C. for 1 hr. After that, 10 U/mL RNase inhibitor, SUPERase-In (Ambion) were added to prevent further reaction from RNase. CMPs were then washed with IMDM and collected by ultracentrifugation at 25000 rpm, 4° C. 60000 of HSCs were cocultured with CMPs, or RNase-treated CMPs, or without CMPs at the concentration of 50 MPs/cell for 8 days in the IMDM medium supplemented with 5% BIT9500, 50 ng/mL rhSCF, but without thrombopoietin. Cell were harvest at d8 for CD41 and DNA staining. Analysis of cell ploidy and CD41 expression and Mk cell number were performed by flow-cytometry (FACSAria II, BD bioscience). HSPCs cocultured with CMPs without RNase treatment became Mks with polyploidy and CD41 positive and the number of Mks with CMPs coculture is higher than Mks of vehicle control. However, here, the number of Mks of both RNase-treated CMPs cocultures decrease, compared to the Mks in CMP coculture (FIG. 21). These data show that the treatment of RNase A/T1 or ONE on CMPs decreases the CMPs ability to induce Mk differentiation of HSCs. Since the function of RNase is to degrade RNA from CMPs, these data show that an optimized RNase treatment can be used to effectively "unload" the native RNA from the MkMPs.

Example 15. Loading of pmaxGFP DNA into CMP or MkMP by Electroporation

To load exogenous material into MP, we choose plasmid DNA as model molecule for loading into MkMPs. There is no prior art on the loading of any microparticles (MkMPs or any other MPs) with exogenous molecules, and thus the following enabling data support our claims for the modification and loading of MkMPs and all MPs with exogenous molecules like DNA, RNA, proteins, non-protein morphogens and drugs. Such loading process could not be anticipated by someone skilled in the art since MPs are very different entities from cells.

Figure 22:
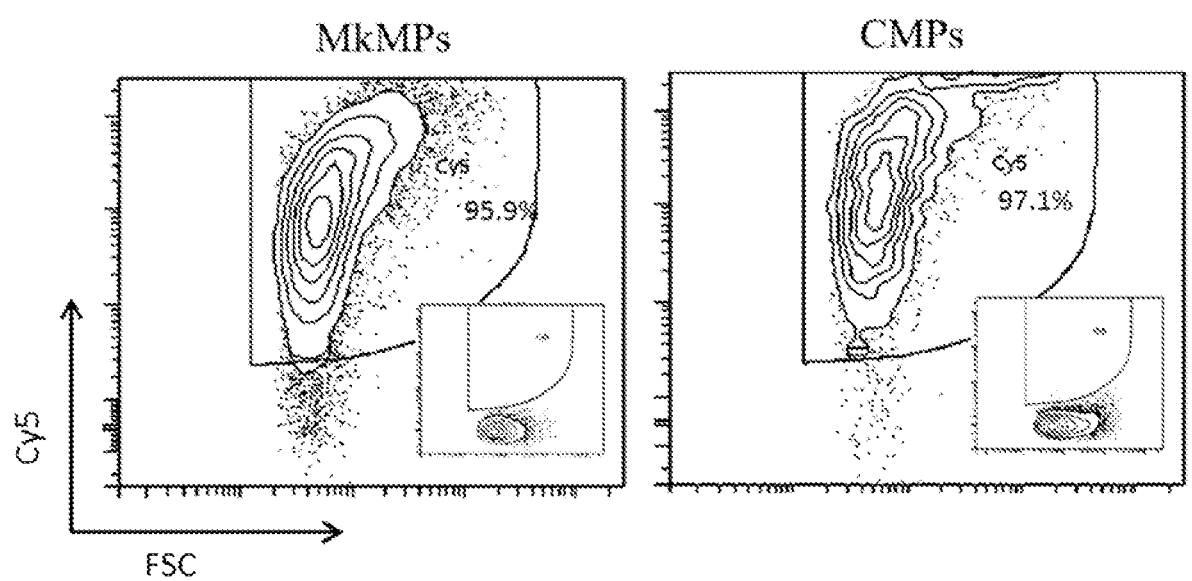
FIG. 22. Flow cytometry analysis of MPs loaded with plasmid DNAs using electroporation. Plasmid DNA, pmaxGFP, were conjugated with red fluorescent dye Cy5. Then plasmids pmaxGFP were loaded into MkMPs and CMPs using electroporation. The resulting MkMPs and CMPs were analyzed by flow cytometry. Electroporation was performed using AMAXA Nucleofector™ II Device. The inserts represent MP without electroporation.
Figure 23:
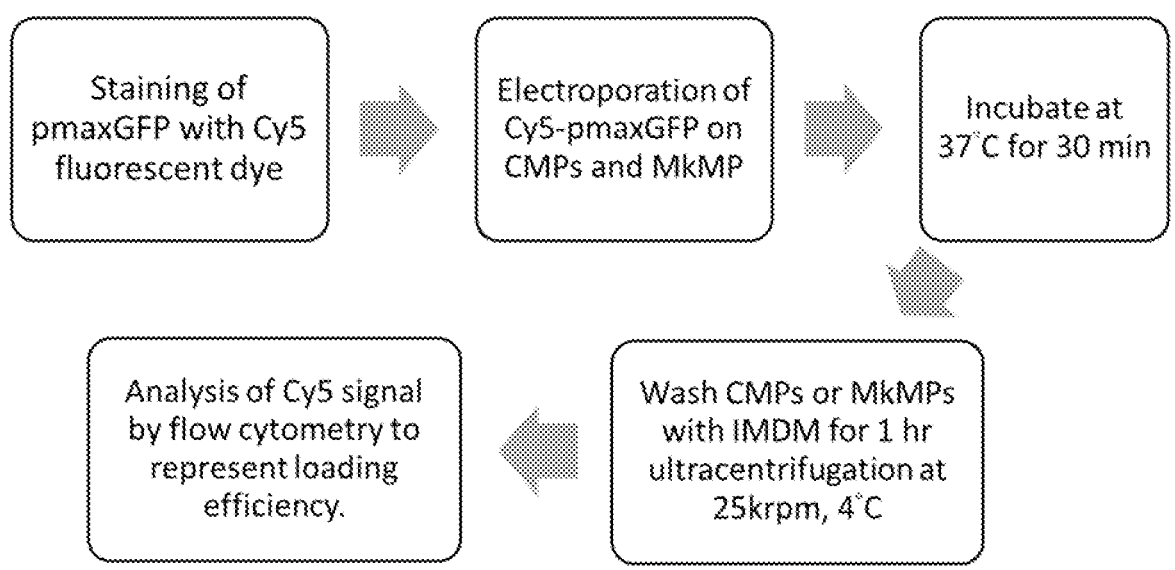
FIG. 23. Brief procedure of loading pmaxGFP DNA by electroporation.

We used a commercially available DNA plasmid (PmaxGFP DNA; Lonza), which we labeled with red fluorescent dye Cy5 using the Label IT® Nucleic Acid Labeling Kit (Mirus) based on the manufacturer's protocol. 2 µg of Cy5-pmaxGFP were electroporated into 10$^6$ CMPs or MkMPs by using AMAXA Nucleofector™ II Device (Lonza) with program T03 or U08, respectively. The procedure of electroporation was followed by manufactural protocol. CMPs or MkMPs were then incubated at 37° C. for 30 min. After 3 times of wash of CMPs or MkMPs with IMDM medium by ultracentrifugation at 25000 rpm, 4° C. for 1 hr each, the loading efficiency of Cy5-pmaxGFP into CMPs or MkMPs were analyzed with flow-cytometry FACSAria II based on Cy5 fluorescence. Electroporation of fluorescent-labeled plasmid DNA (Cy5-pmaxGFP) into MkMPs and CMPs have been performed on AMAXA Nucleofector™ II Device using the specific program U08 and T03, respectively. Base on Cy5 signal, flow-cytometry analysis shows that 95.9% of MkMPs and 97.1% of CMPs were Cy5 positive (FIG. 22), which indicates that both MkMPs and CMPs were loaded with pmaxGFP DNA by electroporation. A summary of the procedure for loading MkMPs and other MPs with exogenous molecules is depicted in FIG. 23. Our data demonstrate that MkMPs and other MPs can be loaded with exogenous molecules and thus methods other than electroporation can be used for carrying out this task. Such methods would include but are not limited to lipofection, virus-mediated transfer, receptor mediated transfer, synthetic particle mediated transfer, and direct injection.

Discussion of Our Disclosed Data for the Support of Our Claims

We show for the first time that shear stress dramatically increased MkMP generation by 30-40 fold. Flaumenhaft et al. demonstrated that the CD41$^+$ MPs in human plasma are mainly derived from Mks rather than activated platelets [5]. When mature Mks enter BM sinusoids and are exposed to shear circulatory forces, numerous MkMPs are likely formed. PMP generation from platelets on immobilized vWF surfaces is also promoted by high shear. While the cellular mechanisms leading to membrane vesiculation and MP release remain an active research field, studies from PMP biogenesis suggest that PS externalization and caspase-3 activation play an important role in MP generation. In our study, we found that caspase-3 activation and PS externalization were enhanced by shear stress, thus suggesting that shear-stress enhanced MkMP generation may be mediated by PS externalization and caspase-3 activation. The latter is supported by the data from the caspase-3 inhibition assays.

The physiological function for MkMPs was also investigated. We demonstrated that MkMPs promote the survival and Mk differentiation of HSPCs in the absence of added TPO. Thus, one possible role for MkMPs in circulation may be to promote differentiation of circulatory HSPCs or perhaps re-enter the hematopoietic BM compartment aiming to target HSPCs for accelerated megakaryopoiesis under stress. Biological roles have been reported previously for other MPs, but never before for MkMPs. For example, MPs generated during macrophage differentiation of THP-1 cells induced differentiation of resting THP-1 cells into macrophages through miRNA-223 transfer [2].

MPs may serve in several different roles in biological processes since bioactive molecules carried by MPs are concentrated and can travel long distances with protection from degradation. Here, we demonstrated that MPs generated by mature Mks induce Mk differentiation of very primitive HSPCs (CD34$^+$Lineage$^-$ cells). In addition, we also investigated if MkMPs could transdifferentiate other types of cells, including MSCs, HUVECs and granulocytes and found out they could not. All of these three types of cells are likely to be in contact with MkMPs in vivo.

We also demonstrated mechanisms through which MkMPs exert their biological effect. Two main questions were examined here: how do MkMPs interact with target cells, and what might be the signaling molecules carried by MkMPs. Three different mechanisms have been reported in the literature to explain how cell-derived MPs and target cells interact. The interaction always starts from MP binding to cells, which requires recognition between receptors and ligands on the membrane surface of MPs and cells. This ligand-receptor recognition is the major reason for the target specificity of MPs. MP binding could be unstable, leading to dissociation of MPs from cell surface, or stable, ending in uptake of MPs by cells. The signaling from temporary or persisting binding of MPs could be enough to regulate cell fate. For example, transfer of CCL5 from PMPs to activated endothelial cells only happens during transient interaction rather than firm attachment between PMPs and endothelial cells under flow condition [6]. It is possible that this temporary binding of MkMPs may have an effect on target HSCs. In addition, we have shown that some MkMPs were taken up by cells through direct fusion and/or endocytosis. After we treated MkMPs with two different RNases to digest the RNA carried by MkMPs, the numbers of Mks with different ploidy levels decreased by half in the coculture with treated MkMPs compared to MkMPs without treatment. This result demonstrates that horizontal transfer of RNA is crucial for the observed biological effect of MkMPs. Transfer of RNA requires uptake of MkMPs by cells following stable binding and thus the RNase treatment results provide additional evidence that MkMPs are taken up by cells. Through confocal microscopy, SEM and TEM analyses of MkMP coculture, we demonstrated that both direct fusion and endocytosis were involved in uptake of MkMPs. Moreover, for the first time, using SEM analysis we dissected the MP fusion process as proceeding through 4 distinct stages. The lamellipodia-like structures during MP fusion were observed and reported for the first time. These results contribute to our limited understanding of MP uptake by cells, which is important regarding the delivery of biological molecules (such as but not limited to RNA, DNA, proteins, lipids) as well other organic molecules and drugs by modified MkMPs for delivery to stem cells. A variety of cellular contents may be delivered to target cells including RNA, DNA, proteins, lipids, phospholipids, non-protein morphogens, non-biological materials, organic molecules, non-organic molecules, synthetic drugs or natural drugs.

It has been reported that MPs have several biological functions and play an essential role in various physiological and pathophysiological processes. Different MPs may have a role in blood coagulation, inflammation, angiogenesis, tumorigenesis, cell differentiation and maturation. Ratajczak et al. showed that MPs from embryonic stem cells (ESCs) when cocultured with hematopoietic progenitor cells (HPCs) result in upregulated expression of early marker of pluripotent (Oct-4, Nanog and Rex-1) and early hematopoietic stem cells (Scl, HoxB4 and GATA 2) markers [7]. Their data suggest that the effect is mediated by RNAs and proteins in the MPs. In another example, MPs from stimulated or apoptotic T lymphocytes harbored sonic hedgehog (Hh) morphogens and were able to induce K562 cells (a cancer cell line) differentiation towards the Mk lineage and promote Mk differentiation of CD34$^+$ HSPCs when cultured in the presence of thrombopoietin [8]. Hh was necessary for these effects. Our invention is very distinct and could not have been anticipated by these findings for several reasons explained in detail below. First, we employ MkMPs and not T-cell derived MPs. Second, our MkMPs do not require Hh morphogens for the effects on HSPCs. Thirdly, this report requires that CD34$^+$ cells are cultured in the presence of TPO, while our invention does not. Fourth, in this report, they show that Hh containing T-cell MPs promote Mk differentiation but not the production of proplatelets or platelets or platelet-like particles.

Mk cells are great sources for MPs since they have much larger cell volume and massive membranes compared to other types of cells. In the present invention, MkMPs are first unloaded from the endogenous RNAs and then reloaded with the desirable RNAs, DNAs, proteins or other molecules for delivery to the target HSPCs. The present invention engineers cell-derived MkMPs where endogenous RNAs are removed from MPs using RNase treatment and exogenous molecules (plasmid DNA here) are loaded into MPs directly using electroporation. This process can be applied to other MPs beyond MkMPs and thus, we disclose for the first time a unique and powerful method for unloading the natural RNA cargo of MPs in order to re-load them with desirable "cargo", i.e., any desirable molecules for delivery to target cells including HSPCs.

In addition to view cell-derived MPs as a tool or a vesicle to deliver therapeutic drugs, MPs from specific cells (like endothelial cells, mesenchymal stem cells or other types) have unique biological function on target cells and other inventors used these MPs as a type of drugs to treat certain types of diseases. In U.S. patent application US 20120321723 A1, the inventors found MPs from stem cells, preferably a bone marrow-mesenchymal stem cell, a glomerular mesenchymal stem cell or a non-oval liver stem cell, exert anti-tumor effect when administered to a tumor patient.

BEST MODE FOR CARRYING OUT THE INVENTION

Figure 24:
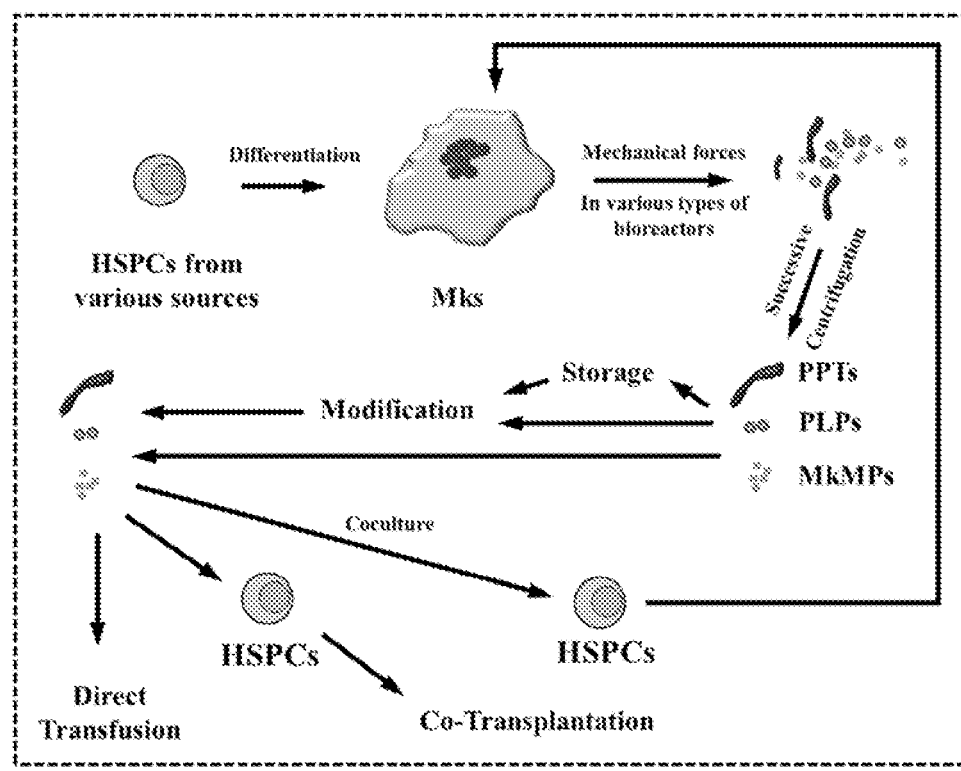
FIG. 24. In this drawing, "Modification" refers to unloading RNAs from MkMPs and/or reloading MkMPs with the desirable RNAs, DNAs, proteins or other therapeutic drugs. HSPCs, hematopoietic stem and progenitor cells; Mks, megakaryocytes; PPT, pro/preplatelets; PLPs, platelet-like particles; MkMPs, megakaryocytic microparticles.

1. Source of Hematopoietic Stem and Progenitor Cells (HSPCs) and Generation of Megakaryocytes (FIG. 24).

Multiple sources of HSPCs, including but not limited to autologous or allogeneic CD34+ cells from bone marrow, peripheral blood or cord blood, are cultured and differentiated to megakaryocytes using a published protocol such as the one published in [9], but many other protocols and their variations can be used. Several such protocols have been disclosed in the scientific and patent literature. HSPCs can be also obtained from embryonic cells or from induced pluripotent stem (iPS) cells.

2. Generation of MkMPs, PLPs or PPTs from Mature or Maturing Megakaryocytes (FIG. 24).

To generate MkMPs or MPs from other cells, shear or other biomechanical forces are applied to the megakaryocytes to generate proplatelets/preplatelets (PPTs), platelet-like particles (PLPs) and megakaryocytic microparticles (MkMPs). The shear flow can be laminar or turbulent and flow application can be carried out in a parallel channel bioreactors, or mixed bioreactor where the cells are either freely suspended or growing on microcarriers (small beads of 100-1000 microns in diameter) where the cells can attach to for growth and maintenance. The intensity of biomechanical forces can be controlled by controlling the flow rate or the agitation/mixing rate as is known to someone skilled in the art, such as in described in Refs. [9-13]. The use of agitated or mixed bioreactors of freely suspended cells or cells attached to microcarriers for producing MPs is disclosed for the first time here. Microcarriers are small particles, mostly spherical but not only, whose surface is appropriately modified for allowing cells to attach and grow on the particle surface. [14, 15] Some microcarriers are also porous allowing cells to grow into the microcarriers. Both types of microcarriers are used for growing cells that require or prefer surface attachment and where the culture can be done both under static conditions but more typically in stirred bioreactors or vessels that enable scale up and quality control by controlling the culture conditions using various sensors such as for pH, dissolved oxygen, nutrient concentrations and metabolite concentrations. [12, 14-16] Tubular or channel bioreactors or microreactors or microfluidic reactors can be used to culture all types of cells and also to expose various human or mammalian cells to biomechanical forces. [13, 16-20] The use of such bioreactors for generating MPs or MVs or any other particle from mammalian or other cells is disclosed for the first time here. The use of such bioreactor systems for generating MPs or MVs or any other particle from mammalian or other cells could not have been anticipated by someone skilled in the art.

3. Separation, Purification and Storage of MkMPs, PLPs, and PPTs but Also MPs from Other Cell Types (FIG. 24).

Three types of particles, PPTs, PLPs and MkMPs, are collected and enriched from static cell culture and flow application using successive differential centrifugations as described in Ref. [9], but several other centrifugation, ultracentrifugation, elutriation, sedimentation and/or membrane protocols can be used as is well known by those skilled in the art [21-24]. MkMPs can be frozen as is known in the art of freezing hematopoietic stem cells for transplantation therapies. [25-27] PLPs or PPTs can either be stored at room temperature or used immediately. PLPs or PPTs can be also frozen using methods as for freezing MkMPs.

4. Modification of MkMPs for the Delivery of "Cargo" Molecules (DNA, RNA, Proteins, Etc) to HSPCs Both In Vivo and Ex Vivo (FIG. 24).

To engineer MkMPs, RNase is used to remove endogenous RNAs inside the microparticles by incubation of RNase and microparticles at 37° C. After that, the desirable RNAs, DNAs, proteins or other therapeutic drugs are loaded into MkMPs using electroporation (e.g., using Nucleofection performed on AMAXA Nucleofector® II Device, Lonza) or lipofection or other methods used in the modification of whole cells, but here applied to MkMPs.

5. Applications of the Produced Unmodified MkMPs, PLPs or PPTs (FIG. 24):

a. Hematopoietic transplantation for the reconstitution of HSPCs in vivo by intravenous infusion or co-infusion with HSPCs, either autologous or allogeneic. This is to enhance the in vivo expansion of HSPCs (by MkMPs), but also the in vivo megakaryopoiesis and platelet biogenesis (by MkMPs, PLPs, and PPTs). The latter two processes are beneficial to patients undergoing chemotherapy or patients with genetic or idiopathic disorders.

b. Ex vivo production of proplatelets or platelets. MkMPs also can be used as differentiation inducing reagent in ex vivo megakaryocytic differentiation and platelet production. The collected PPTs and PLPs can be used in clinical transfusion and intravenously infused to patients who need platelets, including those suffering severe thrombocytopenia disease, idiopathic or due to chemotherapy.

6. Applications of Modified MkMPs (FIG. 24).

The engineered MkMPs can be used in two different ways to deliver desirable materials (DNA, RNA, proteins, morphogens, or drugs) into target cells, including the HSPCs. One way is to infuse these engineered microparticles directly into the patient circulation. The other way is to coculture these microparticles with CD34+ HSPCs or other target cells ex vivo for 2-5 days and then transfuse those cells from coculture into patients.

Although preferred embodiments of the disclosure are illustrated and described in connection with particular features, it will be apparent to those skilled in the art, that the invention can be adapted for use for a wide variety of applications. Various features of the disclosure have been particularly shown and described in connection with illustrated embodiments. However, it must be understood that the particular embodiments merely illustrate and that the invention is to be given its fullest interpretation within the terms of the claims.

The invention claimed is:

1. A method for enhancing platelet biogenesis in a patient in need thereof, comprising administering to the patient isolated CD62P-megakaryocytic microparticles (MkMPs) generated from megakaryocytes, whereby platelet biogenesis in the patient is enhanced.

2. The method of claim 1, wherein the MkMPs are administered to the patient via intravenous infusion.

3. The method of claim 1, wherein the patient suffers thrombocytopenia.

4. The method of claim 1, wherein the patient undergoes chemotherapy.

5. The method of claim 1, wherein the patient has a genetic or idiopathic disorder.

6. The method of claim 1, further comprising enhancing expansion of hematopoietic stem and progenitor cells (HSPCs) in the patient.

7. The method of claim 1, further comprising administering to the patient hematopoietic stem and progenitor cells (HSPCs).

8. The method of claim 7, wherein the HSPCs are administered to the patient via intravenous infusion.

9. The method of claim 1, wherein the MkMPs have a diameter of 100-1000 nm.

10. The method of claim 1, wherein the MkMPs are stored frozen.

11. The method of claim 1, wherein a native RNA, DNA or protein has been removed from the MkMPs.

12. The method of claim 1, wherein the MkMPs are loaded with an exogenous molecule.

13. The method of claim 12, wherein the exogenous molecule is a biological molecule selected from the group consisting of RNAs, DNAs, proteins and lipids.

14. The method of claim 12, wherein the exogenous molecule is a therapeutic drug.

15. The method of claim 12, further comprising loading the MkMPs with the exogenous molecule.

16. The method of claim 12, further comprising unloading a native RNA, DNA or protein from the MkMPs before the MkMPs are loaded with the exogenous molecule.

17. A method for delivery an exogenous molecule into a patient in need thereof, comprising administering to the patient isolated CD62P-megakaryocytic microparticles (MkMPs) generated from megakaryocytes and loaded with an exogenous molecule, and delivering the exogenous molecule to hematopoietic stem and progenitor cells (HSPCs) in the patient, whereby the exogenous molecule is delivered into the patient.

18. The method of claim 17, wherein the MkMPs are administered to the patient via intravenous infusion.

19. The method of claim 17, wherein the MkMPs have a diameter of 100-1000 nm.

20. The method of claim 17, wherein the MkMPs have a diameter of 40-100 nm.

21. The method of claim 17, wherein the exogenous molecule is a biological molecule selected from the group consisting of RNAs, DNAs, proteins and lipids.

22. The method of claim 17, wherein the exogenous molecule is a therapeutic drug.

23. The method of claim 17, further comprising loading the MkMPs with the exogenous molecule.

24. The method of claim 17, further comprising unloading a native RNA, DNA or protein from the MkMPs before the MkMPs are loaded with the exogenous molecule.

25. The method of claim 1, wherein the MkMPs are loaded with an exogenous molecule, the method further comprising delivering the exogenous molecule to hematopoietic stem and progenitor cells (HSPCs) in the patient.

26. The method of claim 17, wherein the patient is in need of enhancing platelet biogenesis.

* * * * *